United States Patent
Gardella et al.

(10) Patent No.: US 11,975,050 B2
(45) Date of Patent: May 7, 2024

(54) PARATHYROID HORMONE POLYPEPTIDE CONJUGATES AND METHODS OF THEIR USE

(71) Applicant: The General Hospital Corporation, Boston, MA (US)

(72) Inventors: Thomas J. Gardella, Needham, MA (US); Ashok Khatri, Charlestown, MA (US); Hiroshi Noda, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/980,944

(22) PCT Filed: Mar. 15, 2019

(86) PCT No.: PCT/US2019/022439
§ 371 (c)(1),
(2) Date: Sep. 15, 2020

(87) PCT Pub. No.: WO2019/178462
PCT Pub. Date: Sep. 19, 2019

(65) Prior Publication Data
US 2020/0405820 A1 Dec. 31, 2020

Related U.S. Application Data

(60) Provisional application No. 62/644,316, filed on Mar. 16, 2018.

(51) Int. Cl.
| | |
|---|---|
| *A61K 38/29* | (2006.01) |
| *A61K 47/54* | (2017.01) |
| *A61K 47/65* | (2017.01) |
| *C07K 14/635* | (2006.01) |

(52) U.S. Cl.
CPC ............ *A61K 38/29* (2013.01); *A61K 47/542* (2017.08); *A61K 47/65* (2017.08); *C07K 14/635* (2013.01)

(58) Field of Classification Search
CPC ...... A61K 38/29; A61K 47/542; A61K 47/65; C07K 14/635
See application file for complete search history.

(56) References Cited

U.S. PATENT DOCUMENTS

| | | | |
|---|---|---|---|
| 5,494,806 A | 2/1996 | Segre et al. | |
| 5,840,853 A | 11/1998 | Segre et al. | |
| 5,886,148 A | 3/1999 | Segre et al. | |
| 6,147,186 A | 11/2000 | Gardella et al. | |
| 6,183,974 B1 | 2/2001 | Bringhurst et al. | |
| 6,362,163 B1 | 3/2002 | Gardella et al. | |
| 6,417,333 B1 | 7/2002 | Bringhurst et al. | |
| 6,495,662 B1 | 12/2002 | Gardella et al. | |
| 6,537,965 B1 | 3/2003 | Bringhurst et al. | |
| 6,541,220 B1 | 4/2003 | Juppner et al. | |
| 6,803,213 B2 | 10/2004 | Bringhurst et al. | |
| 7,022,815 B1 | 4/2006 | Gardella et al. | |
| 7,033,773 B1 | 4/2006 | Bringhurst et al. | |
| 7,057,012 B1 | 6/2006 | Gardella et al. | |
| 7,078,487 B2 | 7/2006 | Juppner et al. | |
| 7,132,260 B2 | 11/2006 | Segre et al. | |
| 7,150,974 B1 | 12/2006 | Segre et al. | |
| 7,153,951 B2 | 12/2006 | Gardella et al. | |
| 7,169,567 B1 | 1/2007 | Gardella et al. | |
| 7,244,834 B2 | 7/2007 | Gardella et al. | |
| 7,371,844 B2 | 5/2008 | Gardella et al. | |
| 7,479,478 B2 | 1/2009 | Bringhurst et al. | |
| 7,521,528 B2 | 4/2009 | Gardella et al. | |
| 7,572,765 B2 | 8/2009 | Gardella | |
| 7,795,220 B2 | 9/2010 | Gardella et al. | |
| 7,910,544 B2 | 3/2011 | Gardella et al. | |
| 7,985,835 B2 | 7/2011 | Gardella et al. | |
| 8,143,374 B2 | 3/2012 | Kronenberg et al. | |
| 8,568,736 B2 | 10/2013 | Gardella et al. | |
| 8,568,737 B2 | 10/2013 | Gardella et al. | |
| 8,603,977 B2 | 12/2013 | Gardella et al. | |
| 9,057,727 B2 | 6/2015 | Gardella et al. | |
| 9,492,508 B2 | 11/2016 | Gardella et al. | |
| 2007/0166276 A1* | 7/2007 | Zhao | A61P 35/00 525/438 |
| 2011/0059892 A1* | 3/2011 | Moussou | A61K 38/29 514/11.8 |
| 2012/0083448 A1 | 4/2012 | Xu et al. | |

(Continued)

FOREIGN PATENT DOCUMENTS

| | | | | |
|---|---|---|---|---|
| CN | 201101448435 A | * | 4/2012 | ............. A61K 38/29 |
| WO | WO-2004/093902 A1 | | 11/2004 | |

(Continued)

OTHER PUBLICATIONS

Extended European Seach Report for European Patent Application No. 19767380.9, dated Jan. 22, 2022 (14 pages).
International Search Report and Written Opinion for International Application No. PCT/US2019/022439, dated Jul. 24, 2019 (57 pages).
Lim et al., "Site-specific fatty acid-conjugation to prolong protein half-life in vivo," J Control Release. 170(2):219-25 (2013).
Liu et al., "Triblock peptide-linker-lipid molecular design improves potency of peptide ligands targeting family B G protein-coupled receptors," Chem Commun (Camb) 51(28):6157-60 (2015).

(Continued)

*Primary Examiner* — Jeffrey E. Russel
(74) *Attorney, Agent, or Firm* — Clark & Elbing LLP

(57) ABSTRACT

Disclosed are peptide-fatty acid conjugates, pharmaceutical compositions containing them, and methods of their medical use in the treatment of, e.g., a disease or condition associated with the PTHR1 signaling overactivity (e.g., hypercalcemia, hypophosphatemia, hyperparathyroidism, or Jansen's chondrodysplasia) or deficiency (e.g., hypoparathyroidism, hyperphosphatemia, osteoporosis, fracture repair, osteomalacia, arthritis, or thrombocytopenia).

7 Claims, 12 Drawing Sheets
Specification includes a Sequence Listing.

(56) References Cited

U.S. PATENT DOCUMENTS

| | | |
|---|---|---|
| 2019/0119348 A1 | 4/2019 | Gardella et al. |
| 2019/0282668 A1* | 9/2019 | Sprogøe .................... A61P 5/20 |
| 2020/0113978 A1* | 4/2020 | Park ....................... A61K 38/29 |

FOREIGN PATENT DOCUMENTS

| | | |
|---|---|---|
| WO | WO-2005/027978 A2 | 3/2005 |
| WO | WO-2010/053548 A2 | 5/2010 |
| WO | WO-2011/143406 A2 | 11/2011 |
| WO | WO-2017/148883 A1 | 9/2017 |
| WO | WO-2017/173372 A1 | 10/2017 |

OTHER PUBLICATIONS

Zorzi et al., "Acylated heptapeptide binds albumin with high affinity and application as tag furnishes long-acting peptides," Nat Commun 8:16092 (2017).
Zorzi et al., "Acylated heptapeptide binds albumin with high affinity and application as tag furnishes long-acting peptides," Nat Commun. 8:16092 (2017) (9 pages).

* cited by examiner

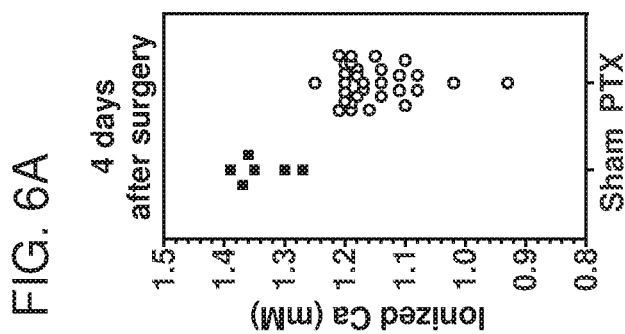

SEQUENCE LISTING

```
<160> NUMBER OF SEQ ID NOS: 11

<210> SEQ ID NO 1
<211> LENGTH: 34
<212> TYPE: PRT
<213> ORGANISM: Artificial Sequence
<220> FEATURE:
<223> OTHER INFORMATION: Synthetic Construct

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 2
<211> LENGTH: 36
<212> TYPE: PRT
<213> ORGANISM: Artificial Sequence
<220> FEATURE:
<223> OTHER INFORMATION: Synthetic Construct

<400> SEQUENCE: 2

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 3
<211> LENGTH: 84
<212> TYPE: PRT
<213> ORGANISM: Homo sapiens

<400> SEQUENCE: 3

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30
```

-continued

Asn Phe Val Ala Leu Gly Ala Pro Leu Ala Pro Arg Asp Ala Gly Ser
            35                  40                  45

Gln Arg Pro Arg Lys Lys Glu Asp Asn Val Leu Val Glu Ser His Glu
 50                  55                  60

Lys Ser Leu Gly Glu Ala Asp Lys Ala Asp Val Asn Val Leu Thr Lys
 65                  70                  75                  80

Ala Lys Ser Gln

<210> SEQ ID NO 4
<211> LENGTH: 34
<212> TYPE: PRT
<213> ORGANISM: Artificial Sequence
<220> FEATURE:
<223> OTHER INFORMATION: Synthetic Construct

<400> SEQUENCE: 4

Trp Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe

<210> SEQ ID NO 5
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Nle
<220> FEATURE:
<221> NAME/KEY: MISC_FEATURE
<222> LOCATION: (6)..(6)
<223> OTHER INFORMATION: Xaa is dTrp

<400> SEQUENCE: 5

Leu Xaa His Gln Leu Xaa Lys Trp Ile Gln Asp Ala Arg Arg Arg Ala
 1               5                  10                  15

Trp Leu His Lys Leu Ile Ala Glu Ile His Thr Ala Glu Ile
            20                  25                  30

<210> SEQ ID NO 6
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Aib
<220> FEATURE:
<221> NAME/KEY: MISC_FEATURE
<222> LOCATION: (3)..(3)
<223> OTHER INFORMATION: Xaa is Aib
<220> FEATURE:
<221> NAME/KEY: MISC_FEATURE
<222> LOCATION: (11)..(11)
<223> OTHER INFORMATION: Xaa is Har

<400> SEQUENCE: 6

Xaa Val Xaa Glu Ile Gln Leu Met His Gln Xaa Ala Lys Trp
 1               5                  10

```
<210> SEQ ID NO 7
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Nle
<220> FEATURE:
<221> NAME/KEY: MISC_FEATURE
<222> LOCATION: (6)..(6)
<223> OTHER INFORMATION: Xaa is dTrp

<400> SEQUENCE: 7

Leu Xaa His Gln Leu Xaa Lys Trp Ile Gln Asp Ala Arg Arg Arg Ala
1               5                   10                  15

Trp Leu Leu Lys Leu Ile Ala Glu Ile His Thr Ala Glu Ile
            20                  25                  30

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is epsilon-palmitoyllysine

<400> SEQUENCE: 8

Glu Tyr Glu Xaa Glu Tyr Glu
1               5

<210> SEQ ID NO 9
<211> LENGTH: 37
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Ser, Trp, Ala, Aib, or absent
<220> FEATURE:
<221> NAME/KEY: MISC_FEATURE
<222> LOCATION: (2)..(2)
<223> OTHER INFORMATION: Xaa is Val or absent
<220> FEATURE:
<221> NAME/KEY: MISC_FEATURE
<222> LOCATION: (3)..(3)
<223> OTHER INFORMATION: Xaa is Ser, Ala, Aib, or absent
<220> FEATURE:
<221> NAME/KEY: MISC_FEATURE
<222> LOCATION: (4)..(4)
<223> OTHER INFORMATION: Xaa is Glu or absent
<220> FEATURE:
<221> NAME/KEY: MISC_FEATURE
<222> LOCATION: (5)..(5)
<223> OTHER INFORMATION: Xaa is Ile, His, or absent
<220> FEATURE:
<221> NAME/KEY: MISC_FEATURE
<222> LOCATION: (6)..(6)
<223> OTHER INFORMATION: Xaa is Gln or absent
<220> FEATURE:
<221> NAME/KEY: MISC_FEATURE
<222> LOCATION: (8)..(8)
<223> OTHER INFORMATION: Xaa is Met, Leu, or Nle
<220> FEATURE:
<221> NAME/KEY: MISC_FEATURE
<222> LOCATION: (10)..(10)
<223> OTHER INFORMATION: Xaa is Asn, Ala, Val, Asp, Glu, or Gln
```

```
<220> FEATURE:
<221> NAME/KEY: MISC_FEATURE
<222> LOCATION: (11)..(11)
<223> OTHER INFORMATION: Xaa is Leu, Ala, Val, Met, Lys, Ile, Arg, Har,
      or Trp
<220> FEATURE:
<221> NAME/KEY: MISC_FEATURE
<222> LOCATION: (12)..(12)
<223> OTHER INFORMATION: Xaa is Gly, Ala, His, Arg, or dTrp
<220> FEATURE:
<221> NAME/KEY: MISC_FEATURE
<222> LOCATION: (13)..(13)
<223> OTHER INFORMATION: Xaa is Lys, Ala, Leu, Gln, Arg, His, or Trp
<220> FEATURE:
<221> NAME/KEY: MISC_FEATURE
<222> LOCATION: (14)..(14)
<223> OTHER INFORMATION: Xaa is His, Leu, Arg, Phe, Trp, or Ser
<220> FEATURE:
<221> NAME/KEY: MISC_FEATURE
<222> LOCATION: (15)..(15)
<223> OTHER INFORMATION: Xaa is Leu or Ile
<220> FEATURE:
<221> NAME/KEY: MISC_FEATURE
<222> LOCATION: (16)..(16)
<223> OTHER INFORMATION: Xaa is Asn or Gln
<220> FEATURE:
<221> NAME/KEY: MISC_FEATURE
<222> LOCATION: (17)..(17)
<223> OTHER INFORMATION: Xaa is Ser or Asp
<220> FEATURE:
<221> NAME/KEY: MISC_FEATURE
<222> LOCATION: (18)..(18)
<223> OTHER INFORMATION: Xaa is Met, Ala, Leu, Glu, Ser, or Phe
<220> FEATURE:
<221> NAME/KEY: MISC_FEATURE
<222> LOCATION: (19)..(19)
<223> OTHER INFORMATION: Xaa is Glu or Arg
<220> FEATURE:
<221> NAME/KEY: MISC_FEATURE
<222> LOCATION: (21)..(21)
<223> OTHER INFORMATION: Xaa is Val or Arg
<220> FEATURE:
<221> NAME/KEY: MISC_FEATURE
<222> LOCATION: (22)..(22)
<223> OTHER INFORMATION: Xaa is Glu, Ala, Phe, Ser, Leu, Asn, Trp, or
      Lys
<220> FEATURE:
<221> NAME/KEY: MISC_FEATURE
<222> LOCATION: (23)..(23)
<223> OTHER INFORMATION: Xaa is Trp, Phe, or Leu
<220> FEATURE:
<221> NAME/KEY: MISC_FEATURE
<222> LOCATION: (25)..(25)
<223> OTHER INFORMATION: Xaa is Arg, His, Leu, Glu, Trp, or Lys
<220> FEATURE:
<221> NAME/KEY: MISC_FEATURE
<222> LOCATION: (26)..(26)
<223> OTHER INFORMATION: Xaa is Lys, His, Ala, Ser, Asn, or Arg
<220> FEATURE:
<221> NAME/KEY: MISC_FEATURE
<222> LOCATION: (27)..(27)
<223> OTHER INFORMATION: Xaa is Lys or Leu
<220> FEATURE:
<221> NAME/KEY: MISC_FEATURE
<222> LOCATION: (28)..(28)
<223> OTHER INFORMATION: Xaa is Leu or Ile
<220> FEATURE:
<221> NAME/KEY: MISC_FEATURE
<222> LOCATION: (29)..(29)
<223> OTHER INFORMATION: Xaa is Gln, Ala, Aib, or absent
<220> FEATURE:
<221> NAME/KEY: MISC_FEATURE
<222> LOCATION: (30)..(30)
<223> OTHER INFORMATION: Xaa is Asp, Glu, Lys, or absent
<220> FEATURE:
<221> NAME/KEY: MISC_FEATURE
<222> LOCATION: (31)..(31)
<223> OTHER INFORMATION: Xaa is Val, Leu, Ile, or absent
<220> FEATURE:
```

```
<221> NAME/KEY: MISC_FEATURE
<222> LOCATION: (33)..(33)
<223> OTHER INFORMATION: Xaa is Asn, Thr, or absent
<220> FEATURE:
<221> NAME/KEY: MISC_FEATURE
<222> LOCATION: (34)..(34)
<223> OTHER INFORMATION: Xaa is Phe, Ala, or absent
<220> FEATURE:
<221> NAME/KEY: MISC_FEATURE
<222> LOCATION: (35)..(35)
<223> OTHER INFORMATION: Xaa is absent or Glu
<220> FEATURE:
<221> NAME/KEY: MISC_FEATURE
<222> LOCATION: (36)..(36)
<223> OTHER INFORMATION: Xaa is absent or Ile
<220> FEATURE:
<221> NAME/KEY: MISC_FEATURE
<222> LOCATION: (37)..(37)
<223> OTHER INFORMATION: Xaa is absent or Cys

<400> SEQUENCE: 9

Xaa Xaa Xaa Xaa Xaa Xaa Leu Xaa His Xaa Xaa Xaa Xaa Xaa Xaa Xaa
1               5                   10                  15

Xaa Xaa Xaa Arg Xaa Xaa Xaa Leu Xaa Xaa Xaa Xaa Xaa Xaa Xaa His
            20                  25                  30

Xaa Xaa Xaa Xaa Xaa
        35

<210> SEQ ID NO 10
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is absent or Ile
<220> FEATURE:
<221> NAME/KEY: MISC_FEATURE
<222> LOCATION: (2)..(2)
<223> OTHER INFORMATION: Xaa is absent or Gln
<220> FEATURE:
<221> NAME/KEY: MISC_FEATURE
<222> LOCATION: (4)..(4)
<223> OTHER INFORMATION: Xaa is Met, Leu, or Nle
<220> FEATURE:
<221> NAME/KEY: MISC_FEATURE
<222> LOCATION: (6)..(6)
<223> OTHER INFORMATION: Xaa is Asn, Ala, Val, Asp, Glu, or Gln
<220> FEATURE:
<221> NAME/KEY: MISC_FEATURE
<222> LOCATION: (7)..(7)
<223> OTHER INFORMATION: Xaa is Leu, Ala, Val, Met, Lys, Ile, Arg, Har,
      or Trp
<220> FEATURE:
<221> NAME/KEY: MISC_FEATURE
<222> LOCATION: (8)..(8)
<223> OTHER INFORMATION: Xaa is Gly, Ala, His, Arg, or dTrp
<220> FEATURE:
<221> NAME/KEY: MISC_FEATURE
<222> LOCATION: (9)..(9)
<223> OTHER INFORMATION: Xaa is Lys, Ala, Leu, Gln, Arg, His, or Trp
<220> FEATURE:
<221> NAME/KEY: MISC_FEATURE
<222> LOCATION: (10)..(10)
<223> OTHER INFORMATION: Xaa is His, Leu, Arg, Phe, Trp, or Ala
<220> FEATURE:
<221> NAME/KEY: MISC_FEATURE
<222> LOCATION: (11)..(11)
<223> OTHER INFORMATION: Xaa is Ile or Leu
<220> FEATURE:
<221> NAME/KEY: MISC_FEATURE
<222> LOCATION: (12)..(12)
<223> OTHER INFORMATION: Xaa is Gln or Asn
```

-continued

```
<220> FEATURE:
<221> NAME/KEY: MISC_FEATURE
<222> LOCATION: (13)..(13)
<223> OTHER INFORMATION: Xaa is Asp or Ser
<220> FEATURE:
<221> NAME/KEY: MISC_FEATURE
<222> LOCATION: (14)..(14)
<223> OTHER INFORMATION: Xaa is Ala, Leu, Met, Glu, Ser, or Phe
<220> FEATURE:
<221> NAME/KEY: MISC_FEATURE
<222> LOCATION: (18)..(18)
<223> OTHER INFORMATION: Xaa is Ala, Phe, Glu, Ser, Leu, Asn, Trp, or
      Lys
<220> FEATURE:
<221> NAME/KEY: MISC_FEATURE
<222> LOCATION: (19)..(19)
<223> OTHER INFORMATION: Xaa is Phe or Trp
<220> FEATURE:
<221> NAME/KEY: MISC_FEATURE
<222> LOCATION: (21)..(21)
<223> OTHER INFORMATION: Xaa is His, Arg, Leu, Trp, or Lys
<220> FEATURE:
<221> NAME/KEY: MISC_FEATURE
<222> LOCATION: (22)..(22)
<223> OTHER INFORMATION: Xaa is Lys, His, Ala, Ser, Asn, or Arg
<220> FEATURE:
<221> NAME/KEY: MISC_FEATURE
<222> LOCATION: (32)..(32)
<223> OTHER INFORMATION: Xaa is Ile, Cys, or Tyr
<220> FEATURE:
<221> NAME/KEY: MISC_FEATURE
<222> LOCATION: (33)..(33)
<223> OTHER INFORMATION: Xaa is absent or Cys

<400> SEQUENCE: 10

Xaa Xaa Leu Xaa His Xaa Xaa Xaa Xaa Xaa Xaa Xaa Xaa Xaa Arg Arg
1               5                   10                  15

Arg Xaa Xaa Leu Xaa Xaa Leu Ile Ala Glu Ile His Thr Ala Glu Xaa
            20                  25                  30

Xaa

<210> SEQ ID NO 11
<211> LENGTH: 36
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Ser, Ala, Trp, or Aib
<220> FEATURE:
<221> NAME/KEY: MISC_FEATURE
<222> LOCATION: (3)..(3)
<223> OTHER INFORMATION: Xaa is Ser, Ala, or Aib
<220> FEATURE:
<221> NAME/KEY: MISC_FEATURE
<222> LOCATION: (5)..(5)
<223> OTHER INFORMATION: Xaa is Ile or His
<220> FEATURE:
<221> NAME/KEY: MISC_FEATURE
<222> LOCATION: (8)..(8)
<223> OTHER INFORMATION: Xaa is Met, Leu, or Nle
<220> FEATURE:
<221> NAME/KEY: MISC_FEATURE
<222> LOCATION: (10)..(10)
<223> OTHER INFORMATION: Xaa is Asn, Ala, Val, Asp, Glu, or Gln
<220> FEATURE:
<221> NAME/KEY: MISC_FEATURE
<222> LOCATION: (11)..(11)
<223> OTHER INFORMATION: Xaa is Leu, Ala, Val, Met, Lys, Ile, Arg, Har,
      or Trp
<220> FEATURE:
<221> NAME/KEY: MISC_FEATURE
<222> LOCATION: (12)..(12)
```

```
<223> OTHER INFORMATION: Xaa is Gly, Ala, His, or Arg
<220> FEATURE:
<221> NAME/KEY: MISC_FEATURE
<222> LOCATION: (13)..(13)
<223> OTHER INFORMATION: Xaa is Lys, Ala, Leu, Gln, Arg, His, or Trp
<220> FEATURE:
<221> NAME/KEY: MISC_FEATURE
<222> LOCATION: (14)..(14)
<223> OTHER INFORMATION: Xaa is His, Leu, Arg, Phe, Trp, or Ser
<220> FEATURE:
<221> NAME/KEY: MISC_FEATURE
<222> LOCATION: (15)..(15)
<223> OTHER INFORMATION: Xaa is Ile or Leu
<220> FEATURE:
<221> NAME/KEY: MISC_FEATURE
<222> LOCATION: (16)..(16)
<223> OTHER INFORMATION: Xaa is Gln or Asn
<220> FEATURE:
<221> NAME/KEY: MISC_FEATURE
<222> LOCATION: (17)..(17)
<223> OTHER INFORMATION: Xaa is Asp or Ser
<220> FEATURE:
<221> NAME/KEY: MISC_FEATURE
<222> LOCATION: (18)..(18)
<223> OTHER INFORMATION: Xaa is Ala, Leu, Met, Glu, Ser, or Phe
<220> FEATURE:
<221> NAME/KEY: MISC_FEATURE
<222> LOCATION: (19)..(19)
<223> OTHER INFORMATION: Xaa is Glu or Arg
<220> FEATURE:
<221> NAME/KEY: MISC_FEATURE
<222> LOCATION: (21)..(21)
<223> OTHER INFORMATION: Xaa is Arg or Val
<220> FEATURE:
<221> NAME/KEY: MISC_FEATURE
<222> LOCATION: (22)..(22)
<223> OTHER INFORMATION: Xaa is Ala, Phe, Glu, Ser, Leu, Asn, Trp, or
      Lys
<220> FEATURE:
<221> NAME/KEY: MISC_FEATURE
<222> LOCATION: (23)..(23)
<223> OTHER INFORMATION: Xaa is Trp, Phe, or Leu
<220> FEATURE:
<221> NAME/KEY: MISC_FEATURE
<222> LOCATION: (25)..(25)
<223> OTHER INFORMATION: Xaa is His, Arg, Leu, Glu, Trp, or Lys
<220> FEATURE:
<221> NAME/KEY: MISC_FEATURE
<222> LOCATION: (26)..(26)
<223> OTHER INFORMATION: Xaa is Lys, His, Ala, Ser, Asn, or Arg
<220> FEATURE:
<221> NAME/KEY: MISC_FEATURE
<222> LOCATION: (27)..(27)
<223> OTHER INFORMATION: Xaa is Lys or Leu
<220> FEATURE:
<221> NAME/KEY: MISC_FEATURE
<222> LOCATION: (28)..(28)
<223> OTHER INFORMATION: Xaa is Leu or Ile
<220> FEATURE:
<221> NAME/KEY: MISC_FEATURE
<222> LOCATION: (29)..(29)
<223> OTHER INFORMATION: Xaa is absent, Gln, Aib, or Ala
<220> FEATURE:
<221> NAME/KEY: MISC_FEATURE
<222> LOCATION: (30)..(30)
<223> OTHER INFORMATION: Xaa is absent, Asp, Lys, or Glu
<220> FEATURE:
<221> NAME/KEY: MISC_FEATURE
<222> LOCATION: (31)..(31)
<223> OTHER INFORMATION: Xaa is absent, Val, Leu, or Ile
<220> FEATURE:
<221> NAME/KEY: MISC_FEATURE
<222> LOCATION: (32)..(32)
<223> OTHER INFORMATION: Xaa is absent or His
<220> FEATURE:
<221> NAME/KEY: MISC_FEATURE
<222> LOCATION: (33)..(33)
<223> OTHER INFORMATION: Xaa is absent, Asn, or Thr
<220> FEATURE:
```

```
<221> NAME/KEY: MISC_FEATURE
<222> LOCATION: (34)..(34)
<223> OTHER INFORMATION: Xaa is absent, Phe, or Ala
<220> FEATURE:
<221> NAME/KEY: MISC_FEATURE
<222> LOCATION: (35)..(35)
<223> OTHER INFORMATION: Xaa is absent or Glu
<220> FEATURE:
<221> NAME/KEY: MISC_FEATURE
<222> LOCATION: (36)..(36)
<223> OTHER INFORMATION: Xaa is absent or Ile

<400> SEQUENCE: 11

Xaa Val Xaa Glu Xaa Gln Leu Xaa His Xaa Xaa Xaa Xaa Xaa Xaa
1               5                   10                  15

Xaa Xaa Xaa Arg Xaa Xaa Xaa Leu Xaa Xaa Xaa Xaa Xaa Xaa Xaa
                20                  25                  30

Xaa Xaa Xaa Xaa
            35
```

PARATHYROID HORMONE POLYPEPTIDE CONJUGATES AND METHODS OF THEIR USE

STATEMENT AS TO FEDERALLY FUNDED RESEARCH

This invention was made with government support under grant numbers P01 11794 and P30 AR066261 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Jun. 21, 2022, is named 51313-002002_Sequence_Listing_6_21_22_ST25 and is 12,151 bytes in size.

FIELD OF THE INVENTION

This invention relates to conjugates including a fatty acid acyl and a parathyroid hormone receptor 1 agonist, antagonist, or inverse agonist. The invention also relates to compositions of the conjugates and methods of their use.

BACKGROUND

Parathyroid hormone receptor 1 (PTHR1) functions as a receptor for parathyroid hormone (PTH) and parathyroid-hormone related protein (PTHrP). PTHR1 is expressed in high levels in bone and kidney and regulates calcium ion homeostasis. Regulation of extracellular calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone indirectly by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D.

Both increased and decreased signaling of PTHR1 are associated with disease. For example, decreased signaling of PTHR1 due to inadequate production of parathyroid hormone (PTH) by the parathyroid glands is associated with the life-long condition hypoparathyroidism. Because PTH is critical for regulation of calcium and phosphate levels, loss of PTH reduces calcium levels in blood and bones and increases phosphate levels (hypocalcemia and hyperphosphatemia). Hypocalcemia leads to symptoms such as neuromuscular irritability, including paresthesias, muscle twitching, laryngeal spasms (which can lead to inability to speak and to alert health providers to the underlying medical condition, which has led to delayed or incorrect treatment), and possibly tetany and seizures. It is the only endocrine disorder in which the missing hormone (namely PTH) is not yet available as therapy.

Excessive signaling activity of parathyroid hormone receptor 1 (PTHR1) is known to be associated with hypercalcemia, hypophosphatemia, hyperparathyroidism, and Jansen's chondrodysplasia. These diseases can arise from overproduction of either of the two endogenous PTHR1 ligands—PTH, as in primary or secondary hyperparathyroidism (HPT), or PTH-related protein (PTHrP), as in humoral hypercalcemia of malignancy. These diseases are characterized by high levels of blood calcium, excessive urinary excretion of calcium and/or phosphate, and can further be associated with abnormal bones, due to alterations in bone formation/resorption activities mediated by PTHR1.

Disruption of calcium homeostasis may produce many clinical conditions (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a parathyroid gland lesion (e.g., adenoma, hyperplasia, or carcinoma). Another type of hypercalcemia, humoral hypercalcemia of malignancy (HHM), is a common paraneoplastic syndrome. It appears to result in most instances from the production by tumors (e.g., squamous, renal, ovarian, or bladder carcinomas) of PTHrP, which appears to mimic certain of the renal and skeletal actions of PTH and is believed to interact with the PTH receptor in these tissues.

PTH(1-34) is a therapeutic in treatment of osteoporosis and conditions of PTH deficiency, namely hypoparathyroidism. PTH(1-34) has been identified as a safe and effective alternative to calcitriol therapy for hypoparathyroidism and is able to maintain normal serum calcium levels without hypercalciuria (Winer et al., J. Clin. Endocrinol. Metab. 88:4214-4220, 2003). Nonetheless, the polypeptide requires injection at least twice daily, and the need in this disease for a long-acting PTH(1-34) analog has therefore been recognized (Winer et al., supra).

Thus, there exists a need for additional PTHR1 agonists, antagonists, and inverse agonists, particularly those that retain high affinity for PTHR1, exhibit prolonged pharmacokinetic and pharmacodynamic properties, and are relatively easy to synthesize and purify.

SUMMARY OF THE INVENTION

In general, the invention provides conjugates including a PTHR1 agonist, antagonist, or inverse agonist peptide and a fatty acid acyl. The fatty acid acyl may be linked to the peptide through a linker of the structure:

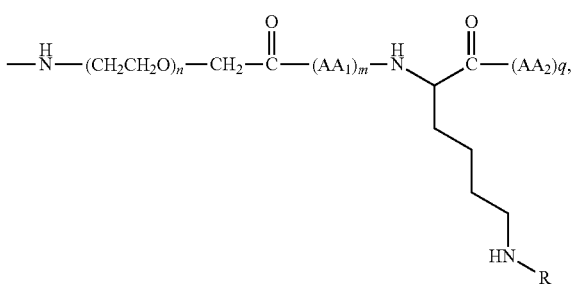

where
n is an integer from 0 to 10;
each of m and q is an integer from 2 to 5;
each $AA_1$ and each $AA_2$ is independently a proteinogenic amino acid; and
R is a bond to the carbonyl carbon of the fatty acid acyl (e.g., a long chain fatty acid acyl).

In some embodiments, the fatty acid acyl is palmitoyl, myristoyl, or stearoyl.

In one aspect, the invention provides a conjugate, or a pharmaceutically acceptable salt thereof, including a fatty acid acyl covalently linked to a PTHR1 agonist, PTHR1 antagonist, or PTHR1 inverse agonist peptide or a fragment thereof containing 14 to 37 (e.g., 24 to 37) contiguous amino acid residues.

In another aspect, the invention provides a conjugate, or a pharmaceutically acceptable salt thereof, containing a polypeptide and a fatty acid acyl covalently linked to the polypeptide, in which the polypeptide contains a sequence of formula (I):

(I)
(SEQ ID NO: 9)
$X_{01}$-$X_{02}$-$X_{03}$-$X_{04}$-$X_{05}$-$X_{06}$-Leu-$X_{08}$-His-$X10$-$X_{11}$-$X_{12}$-$X_{13}$-$X_{14}$-$X_{15}$-$X_{16}$-$X_{17}$-$X_{18}$-$X_{19}$-Arg-$X_{21}$-$X_{22}$-$X_{23}$-Leu-$X_{25}$-$X_{26}$-$X_{27}$-$X_{28}$-$X_{29}$-$X_{30}$-$X_{31}$-His-$X_{33}$-$X_{34}$-$X_{35}$-$X_{36}$-$X_{37}$, where
$X_{01}$ is Ser, Trp, Ala, Aib, or absent;
$X_{02}$ is Val or absent;
$X_{03}$ is Ser, Ala, Aib, or absent;
$X_{04}$ is Glu or absent;
$X_{05}$ is Ile, His, or absent;
$X_{06}$ is Gln, or absent;
$X_{08}$ is Met, Leu, or Nle;
$X_{10}$ is Asn, Ala, Val, Asp, Glu, or Gln;
$X_{11}$ is Leu, Ala, Val, Met, Lys, Ile, Arg, Har, or Trp;
$X_{12}$ is Gly, Ala, His, Arg, or dTrp;
$X_{13}$ is Lys, Ala, Leu, Gln, Arg, His, or Trp;
$X_{14}$ is His, Leu, Arg, Phe, Trp, or Ser;
$X_{15}$ is Leu or Ile;
$X_{16}$ is Asn or Gln;
$X_{17}$ is Ser or Asp;
$X_{18}$ is Met, Ala, Leu, Glu, Ser, or Phe;
$X_{19}$ is Glu or Arg;
$X_{21}$ is Val or Arg;
$X_{22}$ is Glu, Ala, Phe, Ser, Leu, Asn, Trp, or Lys;
$X_{23}$ is Trp, Phe, or Leu;
$X_{25}$ is Arg, His, Leu, Glu, Trp, or Lys;
$X_{26}$ is Lys, His, Ala, Ser, Asn, or Arg;
$X_{27}$ is Lys or Leu;
$X_{28}$ is Leu or Ile;
$X_{29}$ is Gln, Ala, Aib, or absent;
$X_{30}$ is Asp, Glu, Lys, or absent;
$X_{31}$ is Val, Leu, Ile, or absent;
$X_{33}$ is Asn, Thr, or absent;
$X_{34}$ is Phe, Ala, or absent;
$X_{35}$ is absent or Glu;
$X_{36}$ is absent or Ile; and
$X_{37}$ is absent or Cys,
or a fragment thereof containing 14 to 30 (e.g., 24 to 30) contiguous amino acid residues.

In some embodiments, $X_{29}$-$X_{34}$ are not absent. In certain embodiments, $X_{37}$ is absent.

In particular embodiments, the conjugate further contains an additional modification. In some embodiments, the modification is a dye. In certain embodiments, the dye is conjugated to a Lys residue in the peptide or polypeptide.

In some embodiments, the fatty acid acyl is covalently linked to the C-terminus of the peptide or polypeptide.

In particular embodiments, the fatty acid acyl is covalently linked to the peptide or polypeptide through a linker of the structure:

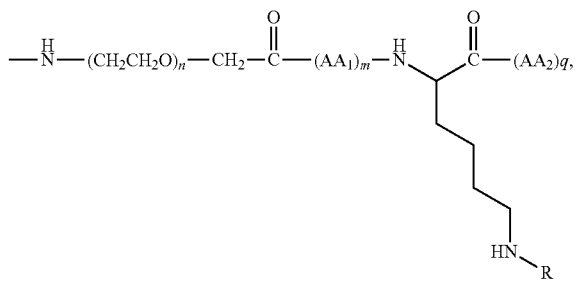

where
n is an integer from 0 to 10;
each of m and q is an integer from 2 to 5;
each $AA_1$ and each $AA_2$ is independently a proteinogenic amino acid; and
R is a bond to the carbonyl carbon of the fatty acid acyl.

In certain embodiments, —C(O)-($AA_1$)$_m$-NH— in the linker structure is —C(O)-EYE-NH— or —C(O)—SYE-NH—.

In certain embodiments, -($AA_2$)$_q$ in the linker structure is -EYE or -ESE. In further embodiments, the C-terminus of -($AA_2$)$_q$ is carboxamide (—$CONH_2$).

In some embodiments, the fatty acid acyl is a very long chain fatty acid or a long chain fatty acid acyl. In particular embodiments, the fatty acid acyl is a long chain fatty acid. In certain embodiments, the long chain fatty acid acyl is palmitoyl.

In particular embodiments, the polypeptide contains a sequence of formula (II):

(II)
(SEQ ID NO: 10)
$X_{05}$-$X_{06}$-Leu-$X_{08}$-His-$X_{10}$-$X_{11}$-$X_{12}$-$X_{13}$-$X_{14}$-$X_{15}$-$X_{16}$-$X_{17}$-$X_{18}$-Arg-Arg-Arg-$X_{22}$-$X_{23}$-Leu-$X_{25}$-$X_{26}$-Leu-Ile-Ala-Glu-Ile-His-Thr-Ala-Glu-$X_{36}$-$X_{37}$, where
$X_{05}$ is absent or Ile;
$X_{06}$ is absent or Gln;
$X_{08}$ is Met, Leu, or Nle;
$X_{10}$ is Asn, Ala, Val, Asp, Glu, or Gln;
$X_{11}$ is Leu, Ala, Val, Met, Lys, Ile, Arg, Har, or Trp;
$X_{12}$ is Gly, Ala, His, Arg, or dTrp;
$X_{13}$ is Lys, Ala, Leu, Gln, Arg, His, or Trp;
$X_{14}$ is His, Leu, Arg, Phe, Trp, or Ala;
$X_{15}$ is Ile or Leu;
$X_{16}$ is Gln or Asn;
$X_{17}$ is Asp or Ser;
$X_{18}$ is Ala, Leu, Met, Glu, Ser, or Phe;
$X_{22}$ is Ala, Phe, Glu, Ser, Leu, Asn, Trp, or Lys;
$X_{23}$ is Phe or Trp;
$X_{25}$ is His, Arg, Leu, Trp, or Lys;
$X_{26}$ is Lys, His, Ala, Ser, Asn, or Arg;
$X_{36}$ is Ile, Cys, or Tyr; and
$X_{37}$ is absent or Cys;

or a fragment thereof containing from 24 to 30 contiguous amino acid residues.

In some embodiments, the polypeptide is a fragment containing amino acid residues 1-32 of formula (II). In further embodiments, the polypeptide is a fragment containing amino acid residues 3-32 of formula (II). In yet further embodiments, the polypeptide is a fragment containing amino acid residues 3-33 of formula (II).

In particular embodiments, $X_{08}$ is Met, $X_{12}$ is Ala, $X_{23}$ is Phe, and $X_{36}$ is Ile. In certain embodiments, $X_{08}$ is Met, $X_{12}$ is dTrp, $X_{23}$ is Trp, and $X_{36}$ is Ile. In further embodiments, $X_{08}$ is Nle, $X_{12}$ is dTrp, $X_{23}$ is Trp, and $X_{36}$ is Tyr. In yet further embodiments, $X_{08}$ is Nle, $X_{12}$ is dTrp, $X_{23}$ is Trp, and $X_{36}$ is Cys. In still further embodiments, $X_{08}$ is Nle, $X_{12}$ is dTrp, $X_{23}$ is Trp, and $X_{36}$ is Ile. In some embodiments, $X_{08}$ is Met, $X_{12}$ is dTrp, $X_{23}$ is Trp, and $X_{36}$ is Ile. In certain embodiments, $X_{08}$ is Nle, $X_{11}$ is Leu, $X_{12}$ is dTrp, and $X_{23}$ is Trp. In further embodiments, $X_{08}$ is Nle, $X_{11}$ is Leu, $X_{12}$ is dTrp, $X_{13}$ is Lys, and $X_{23}$ is Trp.

In certain embodiments, the polypeptide has the amino acid sequence Leu-Nle-His-Gln-Leu-dTrp-Lys-Trp-Ile-Gln-Asp-Ala-Arg-Arg-Arg-Ala-Trp-Leu-His-Lys-Leu-Ile-Ala-Glu-Ile-His-Thr-Ala-Glu-Ile (SEQ ID NO: 5); Leu-Nle-His-Gln-Leu-dTrp-Lys-Trp-Ile-Gln-Asp-Ala-Arg-Arg-Arg-Ala-Trp-Leu-Leu-Lys-Leu-Ile-Ala-Glu-Ile-His-Thr-Ala-Glu-Ile (SEQ ID NO: 7); or a 3-32 or 3-33 fragment thereof.

In some embodiments, the polypeptide is a PTH receptor antagonist or inverse agonist.

In other embodiments, the polypeptide contains a sequence of formula (III):

(III)
(SEQ ID NO: 11)
$X_{01}$-Val-$X_{03}$-Glu-$X_{05}$-Gln-Leu-$X_{08}$-His-$X_{10}$-$X_{11}$-$X_{12}$-$X_{13}$-$X_{14}$-$X_{15}$-$X_{16}$-$X_{17}$-$X_{18}$-$X_{19}$-Arg-$X_{21}$-$X_{22}$-$X_{23}$-Leu-$X_{25}$-$X_{26}$-$X_{27}$-$X_{28}$-$X_{29}$-$X_{30}$-$X_{31}$-$X_{32}$-$X_{33}$-$X_{34}$-$X_{35}$-$X_{36}$, where
$X_{01}$ is Ser, Ala, Trp, or Aib;
$X_{03}$ is Ser, Ala, or Aib;
$X_{05}$ is Ile or His;
$X_{08}$ is Met, Leu, or Nle;
$X_{10}$ is Asn, Ala, Val, Asp, Glu, or Gln;
$X_{11}$ is Leu, Ala, Val, Met, Lys, Ile, Arg, Har, or Trp;
$X_{12}$ is Gly, Ala, His, or Arg;
$X_{13}$ is Lys, Ala, Leu, Gln, Arg, His, or Trp;
$X_{14}$ is His, Leu, Arg, Phe, Trp, or Ser;
$X_{15}$ is Ile or Leu;
$X_{16}$ is Gln or Asn;
$X_{17}$ is Asp or Ser;
$X_{18}$ is Ala, Leu, Met, Glu, Ser, or Phe;
$X_{19}$ is Glu or Arg;
$X_{21}$ is Arg or Val;
$X_{22}$ is Ala, Phe, Glu, Ser, Leu, Asn, Trp, or Lys;
$X_{23}$ is Trp, Phe, or Leu;
$X_{25}$ is His, Arg, Leu, Glu, Trp, or Lys; and
$X_{26}$ is Lys, His, Ala, Ser, Asn, or Arg;
$X_{27}$ is Lys or Leu;
$X_{28}$ is Leu or Ile;
$X_{29}$ is absent, Gln, Aib, or Ala;
$X_{30}$ is absent, Asp, Lys, or Glu;
$X_{31}$ is absent, Val, Leu, or Ile;
$X_{32}$ is absent or His;
$X_{33}$ is absent, Asn, or Thr;
$X_{34}$ is absent, Phe, or Ala;
$X_{35}$ is absent or Glu; and
$X_{36}$ is absent or Ile;

or a fragment thereof containing from 14 to 30 (e.g., 28 to 30) contiguous amino acid residues.

In some embodiments, $X_{35}$ and $X_{36}$ are absent. In certain embodiments, $X_{01}$ and $X_{03}$ are Ala; $X_{10}$ is Gln; $X_{11}$ is Arg; $X_{12}$ is Ala; and $X_{14}$ is Trp. In particular embodiments, $X_{01}$ is Ala; $X_{03}$ is Aib; $X_{10}$ is Gln; $X_{11}$ is Har; $X_{12}$ is Ala; and $X_{14}$ is Trp. In further embodiments, $X_{01}$ is Trp. In yet further embodiments, $X_{18}$ is Ala; $X_{22}$ is Ala; or $X_{26}$ is Lys. In still further embodiments, $X_{18}$ is Ala; $X_{22}$ is Ala; and $X_{26}$ is Lys.

In particular embodiments, the polypeptide has the amino acid sequence:

(SEQ ID NO: 1)
Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe;

(SEQ ID NO: 4)
Trp-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe;

(SEQ ID NO: 6)
Aib-Val-Aib-Glu-Ile-Gln-Leu-Met-His-Gln-Har-Ala-Lys-Trp;

or a fragment thereof containing from 14 to 30 (e.g., 28 to 30) contiguous amino acid residues.

In some embodiments, the polypeptide is hPTH(1-84) or a fragment thereof containing 28 to 34 contiguous N-terminal amino acids.

In certain embodiments, the polypeptide is a PTH receptor agonist.

In yet another aspect, the invention provides a pharmaceutical composition containing a conjugate of the invention and one or more pharmaceutically acceptable carriers or excipients.

In a further aspect, the invention provides a method of modulating the activity of parathyroid hormone receptor 1 (PTHR1) in a cell by contacting the cell with a conjugate of the invention or a pharmaceutical composition of the invention.

In another aspect, the invention provides a method of antagonizing or inversely agonizing the activity of PTHR1 in a cell by contacting the cell with a conjugate of the invention or a pharmaceutical composition of the invention.

In yet another aspect, the invention provides a method of agonizing the activity of PTHR1 in a cell by contacting the cell with a conjugate of the invention or a pharmaceutical composition of the invention.

In some embodiments of any of the foregoing aspects, the cell is a human cell.

In a further aspect, the invention provides a method of treating a subject with a disease or condition associated with PTHR1 signaling overactivity by administering to the subject an effective amount of a conjugate of the invention or a pharmaceutical composition of the invention.

In some embodiments, the disease or condition is hypercalcemia, hypophosphatemia, hyperparathyroidism, or Jansen's chondrodysplasia. In certain embodiments, the conjugate or pharmaceutical composition is administered in an amount sufficient to reduce PTHR1 signaling.

In another aspect, the invention provides a method of treating a subject having a disease selected from the group consisting of hypoparathyroidism, hyperphosphatemia, osteoporosis, fracture repair, osteomalacia, arthritis, thrombocytopenia, and chronic kidney disease by administering to the subject a conjugate of the invention or a pharmaceutical composition of the invention in an amount sufficient to treat said disease.

In some embodiments, the administering includes subcutaneous, intravenous, intranasal, transpulmonary, transdermal, transmucosal, or oral administration of the conjugate or pharmaceutical composition to the subject.

In some embodiments of any of the foregoing aspects, the polypeptide is fewer than 50 amino acids in length.

Other features and advantages of the invention will be apparent from the following detailed description, the drawings, and the claims.

Definitions

The term "dye" is used herein to mean an agent known in the art to be useful in the imaging of biological systems (e.g., a fluorescent dye (e.g., tetramethylrhodamine)).

The term "effective amount," when used in reference to treating a condition or disease (e.g., a disease associated with the PTHR1 signaling overactivity (e.g., hypercalcemia, hypophosphatemia, hyperparathyroidism, or Jansen's chondrodysplasia) or deficiency (e.g., hypoparathyroidism, hyperphosphatemia, osteoporosis, fracture repair, osteomalacia, arthritis, or thrombocytopenia)), refers to an amount of a conjugate of the invention or a pharmaceutically acceptable salt thereof that treats the condition or disease in a subject.

The term "endogenous agonist" of a parathyroid hormone receptor 1 (PTHR1) is used herein to mean a compound produced by an organism, or a synthetic phenocopy of that compound, i.e., a compound having the same pharmacological activity as the endogenous agonist. For example, the native PTH peptide is (1-84), and PTHrP is ~(1-140) amino acids; phenocopies of these ligands include PTH(1-34) and PTHrP(1-36), respectively. An endogenous agonist is involved in or modulates the normal physiological activation of the PTHR1. PTHR1 has multiple endogenous agonists (e.g., PTH and PTHrP).

The term "fatty acid," as used herein, represents a linear, saturated, acyclic, aliphatic carboxylic acid having 4 to 28 carbon atoms. A "long chain fatty acid" is a fatty acid having 13 to 21 carbon atoms (e.g., 14 to 18 carbon atoms), and a "very long chain fatty acid" is a fatty acid having 22 to 28 carbon atoms.

The term "fatty acid acyl," as used herein, represents a monovalent group that is a fatty acid having a carboxylic hydroxyl replaced with a valency. Non-limiting examples of long chain fatty acids include myristic acid, palmitic acid, and stearic acid.

The term "fragment," when used in reference to peptides, refers to a portion of the peptide. Thus, a 1-n polypeptide fragment refers to a polypeptide having a sequence that starts at the first N-terminal amino acid residue of the polypeptide and ends at the $n^{th}$ amino acid residue of the polypeptide.

Similarly, a 3-n polypeptide fragment refers to a polypeptide having a sequence that starts at the third N-terminal amino acid residue of the polypeptide and ends at the $n^{th}$ amino acid residue of the polypeptide.

The terms "polypeptide" and "peptide" are used interchangeably herein to mean a compound that contains a sequence of amino acids bonded to each other through peptidic bonds. A polypeptide or peptide includes at least 10 amino acids.

The term "PTHR1" is used herein to mean a parathyroid hormone receptor 1 (e.g., a human parathyroid hormone receptor 1 (hPTHR1)). PTHR1 may be wild-type or may be a naturally-occurring mutant PTHR1 which has constitutive activity (e.g., PTHR1 expressed in cells of a subject having Jansen's chondrodysplasia). For example, a naturally-occurring mutant PTHR1 which has constitutive activity can be PTHR1-H223R or PTHR1-T410P.

The term "PTHR1 agonist" is used herein to mean a conjugate or polypeptide capable of binding PTHR1 having a constitutive activity and, upon binding, increasing the activity of PTHR1. The activity of PTHR1 agonist may be assessed using methods known in the art for assessing agonist activity or using methods described herein.

The term "PTHR1 antagonist" is used herein to mean a conjugate or polypeptide capable of binding PTHR1, thereby blocking or dampening endogenous agonist-mediated responses without agonizing the signaling activity of PTHR1. The activity of PTHR1 antagonist may be assessed using methods known in the art for assessing antagonist activity or using methods described herein.

The term "PTHR1 inverse agonist" is used herein to mean a conjugate or polypeptide capable of binding PTHR1 having a constitutive activity and, upon binding, reducing the constitutive activity of PTHR1. The activity of PTHR1 inverse agonist may be assessed using methods known in the art for assessing inverse agonist activity or using methods described herein.

The term "radionuclide" is used herein to mean a radioactive isotope known in the art to be useful in imaging of biological systems.

The term "subject" is used herein to mean a mammal (e.g., a human) diagnosed by a medical practitioner as having a condition or disease, e.g., a disease associated with the PTHR1 signaling overactivity (e.g., hypercalcemia, hypophosphatemia, hyperparathyroidism, or Jansen's chondrodysplasia) or deficiency (e.g., hypoparathyroidism, hyperphosphatemia, osteoporosis, fracture repair, osteomalacia, arthritis, or thrombocytopenia). Diagnosis may be performed by techniques and methods known in the art. A subject to be treated according to the methods of the invention may have been subjected to standard tests (e.g., tests for serum calcium levels or serum phosphate levels) or may have been identified, without such tests, as one at high risk due to the presence of one or more risk factors (e.g., diseases associated with elevated serum calcium levels (e.g., cancer, tuberculosis, and sarcoidosis) and therapeutic regimens increasing the release of parathyroid hormone (e.g., lithium) or reducing serum phosphate levels (e.g., antacids)).

The terms "treating" or "treatment," when used herein in reference to a subject, are used herein to mean ameliorating at least one symptom of a condition or disease in a subject having the condition or disease, e.g., a disease associated with the PTHR1 signaling overactivity (e.g., hypercalcemia, hypophosphatemia, hyperparathyroidism, or Jansen's chondrodysplasia) or deficiency (e.g., hypoparathyroidism, hyperphosphatemia, osteoporosis, fracture repair, osteomalacia, arthritis, or thrombocytopenia), as compared with an equivalent untreated control. Such reduction in the symptom (e.g., a reduction in serum calcium levels or an increase in serum phosphate levels, or vice versa) is at least 5% (e.g., at least 10%, 20%, 40%, 50%, 60%, 80%, 90%, 95%, or 100%), as measured in accordance with methods recognized in the art as suitable for assessing the symptom (e.g., serum calcium or phosphate levels).

Unless defined otherwise, all technical and scientific terms used herein have the same meaning as commonly understood to one of ordinary skill in the art to which this disclosure belongs. For any term present in the art which is identical to any term expressly defined in this disclosure, the term's definition presented in this disclosure will control in all respects. Although methods and materials similar or equivalent to those described herein can be used in the practice of the disclosed methods and compositions, the exemplary methods and materials are described herein.

BRIEF DESCRIPTION OF THE DRAWINGS

FIGS. 6A, 6B, and 6C are graphs showing blood calcium levels in mice after parathyroidectomy (FIG. 6A) and blood calcium levels (FIG. 6B) and 1,25(OH)$_2$-vitamin D levels (FIG. 6C) after injection with vehicle, PTH(1-34) (#2009), or Palm-PTH(1-34) (#2027).

DETAILED DESCRIPTION

Figure 1:
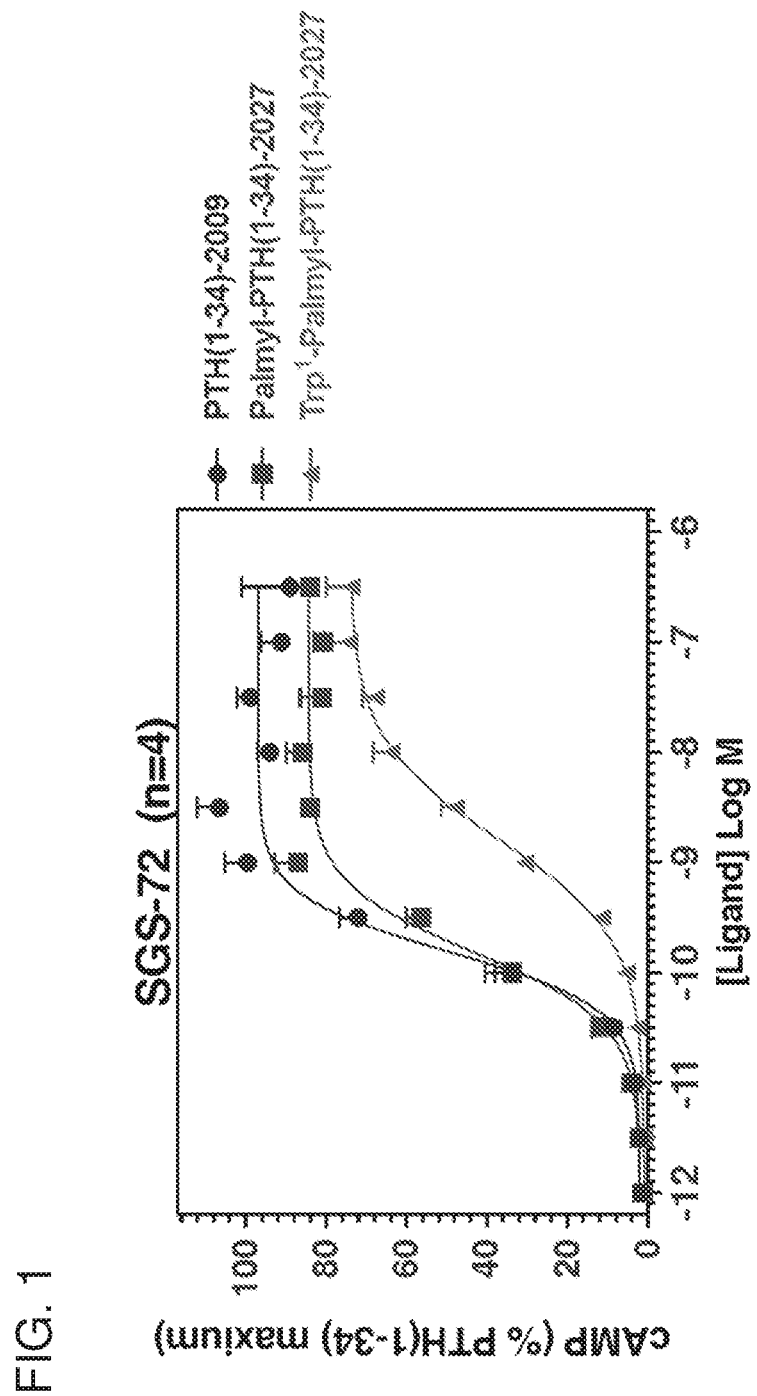
FIG. 1 is a graph showing dose-dependent activation of cAMP signaling in SaOS2/glosensor (SGS-72) cells. Cells were treated with the indicated doses of PTH(1-34) (#2009), Palm-PTH(1-34) (#2027), or Trp$^1$-Palm-PTH(1-34) (#2029) and cAMP was measured as luminescence. The cells are derived from the human osteoblast cell line, SaOS2 by stable transfection with a glosensor cAMP reporter. Shown are mean data (±SEM) of four experiments. Curve fit parameters are reported in Table 2.

In general, the present invention provides conjugates including a PTHR1 agonist, antagonist, or inverse agonist peptide and a fatty acid acyl. The fatty acid acyl may be linked to the peptide through a linker of the structure:

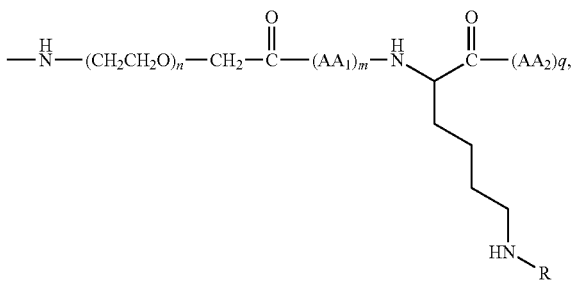

where
n is an integer from 0 to 10;
each of m and q is an integer from 2 to 5;
each $AA_1$ and each $AA_2$ is independently a proteinogenic amino acid; and
R is a bond to the carbonyl carbon of the fatty acid acyl (e.g., a long chain fatty acid acyl).

In some embodiments, the fatty acid acyl is palmitoyl, myristoyl, or stearoyl.

Advantageously, conjugates of the invention may exhibit superior pharmacokinetic properties (e.g., $t_{1/2}$, AUC, and $C_{max}$). Without wishing to be bound by theory, it is believed that a conjugate of the invention may form a complex with serum albumin upon administration to a subject, thereby reducing the clearance of the PTHR1 agonist, antagonist, or inverse agonist peptide from the subject. The superior pharmacokinetic properties of conjugates of the invention may advantageously reduce the need for frequent administration of unconjugated peptides (e.g., PTH(1-34)). For example, a dosing regimen of a conjugate including a fatty acid acyl and a PTHR1 agonist, antagonist, or inverse agonist peptide may be, e.g., once daily, instead of multiple administrations per day, as is typically needed for PTH(1-34).

The enhanced pharmacokinetics of the conjugates of the invention may be achieved without the use of modifications including long polyethylene glycol (PEG) chains, thereby facilitating preparation, purification, and/or characterization, as the conjugates of the invention are typically mono-dispersed, whereas polypeptides linked to long PEG chains are difficult to produce and purify as mono-dispersed compositions because of the heterogeneity of the PEG compositions and the steric effects of the PEG chains on peptide coupling. Thus, conjugates of the invention may include short PEG chains (e.g., in the linker connecting the polypeptide to the fatty acid acyl), such as $PEG_2$ to $PEG_{10}$ (preferably, $PEG_2$).

The polypeptides may include or may be a sequence of formula (I):

(I)

(SEQ ID NO: 9)
$X_{01}$-$X_{02}$-$X_{03}$-$X_{04}$-$X_{05}$-$X_{06}$-Leu-$X_{08}$-His-X10-$X_{11}$-$X_{12}$-$X_{13}$-$X_{14}$-$X_{15}$-$X_{16}$-$X_{17}$-$X_{18}$-$X_{19}$-Arg-$X_{21}$-$X_{22}$-$X_{23}$-Leu-$X_{25}$-$X_{26}$-$X_{27}$-$X_{28}$-$X_{29}$-$X_{30}$-$X_{31}$-His-$X_{33}$-$X_{34}$-$X_{35}$-$X_{36}$-$X_{37}$, wherein
$X_{01}$ is Ser, Trp, Ala, Aib, or absent;
$X_{02}$ is Val or absent;
$X_{03}$ is Ser, Ala, Aib, or absent;
$X_{04}$ is Glu or absent;
$X_{05}$ is Ile, His, or absent;
$X_{06}$ is Gln, or absent;
$X_{08}$ is Met, Leu, or Nle;
$X_{10}$ is Asn, Ala, Val, Asp, Glu, or Gln;
$X_{11}$ is Leu, Ala, Val, Met, Lys, Ile, Arg, Har, or Trp;
$X_{12}$ is Gly, Ala, His, Arg, or dTrp;
$X_{13}$ is Lys, Ala, Leu, Gln, Arg, His, or Trp;
$X_{14}$ is His, Leu, Arg, Phe, Trp, or Ser;
$X_{15}$ is Leu or Ile;
$X_{16}$ is Asn or Gln;
$X_{17}$ is Ser or Asp;
$X_{18}$ is Met, Ala, Leu, Glu, Ser, or Phe;
$X_{19}$ is Glu or Arg;
$X_{21}$ is Val or Arg;
$X_{22}$ is Glu, Ala, Phe, Ser, Leu, Asn, Trp, or Lys;
$X_{23}$ is Trp, Phe, or Leu;
$X_{25}$ is Arg, His, Leu, Glu, Trp, or Lys;
$X_{26}$ is Lys, His, Ala, Ser, Asn, or Arg;
$X_{27}$ is Lys or Leu;
$X_{28}$ is Leu or Ile;
$X_{29}$ is Gln, Ala, Aib, or absent;
$X_{30}$ is Asp, Glu, Lys, or absent;
$X_{31}$ is Val, Ile, Leu, or absent;
$X_{33}$ is Asn, Thr, or absent;
$X_{34}$ is Phe, Ala, or absent;
$X_{35}$ is absent or Glu;
$X_{36}$ is absent or Ile; and
$X_{37}$ is absent or Cys,
or a fragment thereof comprising 14 to 30 (e.g., 24 to 30) contiguous amino acid residues.

In some embodiments, a fragment of a polypeptide of formula (I) is a peptide including from 30 to 32 contiguous amino acid residues. In certain embodiments, a fragment of a polypeptide of formula (I) is a peptide including amino acid residues 1-32 of formula (I), amino acid residues 3-32 of formula (I), or amino acid residues 3-33 of formula (I).

The conjugates including PTHR1 antagonist or inverse agonist peptides can be used in a method of treating a condition or a disease of the PTHR1 signaling overactivity (e.g., hypercalcemia, hypophosphatemia, hyperparathyroidism, Jansen's chondrodysplasia, and chronic kidney disease). These diseases are typically associated with higher than normal serum levels of calcium, with lower than normal serum levels of phosphate, with higher than normal levels of endogenous PTHR1 agonist(s), or with constitutive activity of PTHR1 mutants. The peptide included in the conjugate of the invention may include or may be a sequence of formula (II):

(II)
(SEQ ID NO: 10)
$X_{05}$-$X_{06}$-Leu-$X_{08}$-His-$X_{10}$-$X_{11}$-$X_{12}$-$X_{13}$-$X_{14}$-$X_{15}$-$X_{16}$-$X_{17}$-$X_{18}$-Arg-Arg-Arg-$X_{22}$-$X_{23}$-Leu-$X_{25}$-$X_{26}$-Leu-Ile-Ala-Glu-Ile-His-Thr-Ala-Glu-$X_{36}$-$X_{37}$, where
$X_{05}$ is absent or Ile;
$X_{06}$ is absent or Gln;
$X_{08}$ is Met, Leu, or Nle;
$X_{10}$ is Asn, Ala, Val, Asp, Glu, or Gln;
$X_{11}$ is Leu, Ala, Val, Met, Lys, Ile, Arg, Har, or Trp;
$X_{12}$ is Gly, Ala, His, Arg, or dTrp;
$X_{13}$ is Lys, Ala, Leu, Gln, Arg, His, or Trp;
$X_{14}$ is His, Leu, Arg, Phe, Trp, or Ala;
$X_{15}$ is Ile or Leu;
$X_{16}$ is Gln or Asn;
$X_{17}$ is Asp or Ser;
$X_{18}$ is Ala, Leu, Met, Glu, Ser, or Phe;
$X_{22}$ is Ala, Phe, Glu, Ser, Leu, Asn, Trp, or Lys;
$X_{23}$ is Phe or Trp;
$X_{25}$ is His, Arg, Leu, Trp, or Lys;
$X_{26}$ is Lys, His, Ala, Ser, Asn, or Arg;
$X_{36}$ is Ile, Cys, or Tyr; and
$X_{37}$ is absent or Cys;
or a fragment thereof comprising from 24 to 30 contiguous amino acid residues.

In some embodiments, $X_{08}$ is Nle. In further embodiments, $X_{12}$ is dTrp. In yet further embodiments, $X_{23}$ is Trp. In still further embodiments, $X_{10}$ is Asn or Gln. In other embodiments, $X_{11}$ is Leu or Arg. In yet other embodiments, $X_{12}$ is dTrp, Gly, or Ala. In certain embodiments, $X_{13}$ is Lys. In particular embodiments, $X_{14}$ is His or Trp. In some embodiments, $X_{18}$ is Ala or Met. In further embodiments, $X_{22}$ is Ala or Glu. In yet further embodiments, $X_{25}$ is Arg or His. In still further embodiments, $X_{26}$ is Lys.

The conjugates including PTHR1 agonist peptides can be used in a method of treating a condition or a disease of the PTHR1 signaling deficiency (e.g., hypoparathyroidism, hyperphosphatemia, osteoporosis, fracture repair, osteomalacia, arthritis, or thrombocytopenia). The peptide included in the conjugate of the invention may include or may be a sequence of formula (III):

(III)
(SEQ ID NO: 11)
$X_{01}$-Val-$X_{03}$-Glu-$X_{05}$-Gln-Leu-$X_{08}$-His-$X_{10}$-$X_{11}$-$X_{12}$-$X_{13}$-$X_{14}$-$X_{15}$-$X_{16}$-$X_{17}$-$X_{18}$-$X_{19}$-Arg-$X_{21}$-$X_{22}$-$X_{23}$-Leu-$X_{25}$-$X_{26}$-$X_{27}$-$X_{28}$-$X_{29}$-$X_{30}$-$X_{31}$-$X_{32}$-$X_{33}$-$X_{34}$-$X_{35}$-$X_{36}$, where
$X_{01}$ is Ser, Ala, Trp, or Aib;
$X_{03}$ is Ser, Ala, or Aib;
$X_{05}$ is Ile or His;
$X_{08}$ is Met, Leu, or Nle;
$X_{10}$ is Asn, Ala, Val, Asp, Glu, or Gln;
$X_{11}$ is Leu, Ala, Val, Met, Lys, Ile, Arg, Har, or Trp;
$X_{12}$ is Gly, Ala, His, or Arg;
$X_{13}$ is Lys, Ala, Leu, Gln, Arg, His, or Trp;
$X_{14}$ is His, Leu, Arg, Phe, Trp, or Ser;
$X_{15}$ is Ile or Leu;
$X_{16}$ is Gln or Asn;
$X_{17}$ is Asp or Ser;
$X_{18}$ is Ala, Leu, Met, Glu, Ser, or Phe;
$X_{19}$ is Glu or Arg;
$X_{21}$ is Arg or Val;
$X_{22}$ is Ala, Phe, Glu, Ser, Leu, Asn, Trp, or Lys;
$X_{23}$ is Trp, Phe, or Leu;
$X_{25}$ is His, Arg, Leu, Glu, Trp, or Lys; and
$X_{26}$ is Lys, His, Ala, Ser, Asn, or Arg;
$X_{27}$ is Lys or Leu;
$X_{28}$ is Leu or Ile;
$X_{29}$ is absent, Gln, Aib, or Ala;
$X_{30}$ is absent, Asp, Lys, or Glu;
$X_{31}$ is absent, Val, Leu, or Ile;
$X_{32}$ is absent or His;
$X_{33}$ is absent, Asn, or Thr;
$X_{34}$ is absent, Phe, or Ala;
$X_{35}$ is absent or Glu; and
$X_{36}$ is absent or Ile;

or a fragment thereof comprising from 14 to 30 (e.g., 28 to 30) contiguous amino acid residues.

In some embodiments, $X_{08}$ is Nle. In further embodiments, $X_{12}$ is dTrp. In yet further embodiments, $X_{23}$ is Trp. In still further embodiments, $X_{10}$ is Asn or Gln. In other embodiments, $X_{11}$ is Leu or Arg. In yet other embodiments, $X_{12}$ is dTrp, Gly, or Ala. In certain embodiments, $X_{13}$ is Lys. In particular embodiments, $X_{14}$ is His or Trp. In some embodiments, $X_{18}$ is Ala or Met. In further embodiments, $X_{22}$ is Ala or Glu. In yet further embodiments, $X_{25}$ is Arg or His. In still further embodiments, $X_{26}$ is Lys. In other embodiments, the peptide includes or is hPTH(1-34) (SEQ ID NO:1). In yet other embodiments, the peptide includes or is hPTHrP(1-36) (SEQ ID NO:2). In still other embodiments, the peptide includes or is hPTH(1-84) (SEQ ID NO:3).

Exemplary peptides and their conjugates are listed in Table 1.

producing human PTH on a relatively large scale has been reported in Goud et al., J. Bone Min. Res. 6:781, 1991. The peptide chemical synthesis approach generally entails the use of automated synthesizers and appropriate resin as solid phase, to which the C-terminal amino acid of a desired polypeptide is attached. Extension of the peptide in the N-terminal direction is then achieved by successively coupling a suitably protected form of the next desired amino acid, typically using chemical protocols based on amino-protecting groups (e.g., Fmoc- or Boc-based), until synthesis is complete. Protecting groups are then cleaved from the peptide, usually with concomitant cleavage of the peptide from the resin, and the peptide is then isolated and purified using conventional techniques, such as by reversed phase HPLC using appropriate mobile phase (e.g., acetonitrile as solvent and tri-fluoroacetic acid as an ion-pairing agent). Such procedures are generally described in numerous publications and reference may be made, for example, to

TABLE 1

| SEQ ID NO. | Ref. No. | Chemical Name | Sequence |
|---|---|---|---|
| 1 | 2009 | PTH(1-34) | SVSEIQLMHNLGKHLNSMERVEWLRKKLQDVHNF-NH₂ |
| 1 | 2010 | TMR-PTH(1-34) | SVSEIQLMHNLGK'HLNSMERVEWLRKKLQDVHNF-NH₂ |
| 1 | 2027 | Palm-PTH(1-34) | SVSEIQLMHNLGKHLNSMERVEWLRKKLQDVHNF-(PEG)₂-EYEK(palm)EYE-NH₂ |
| 1 | 2028 | TMR-Palm-PTH(1-34) | SVSEIQLMHNLGK'HLNSMERVEWLRKKLQDVHNF-(PEG)₂-EYEK(palm)EYE-NH₂ |
| 4 | 2029 | W1-Palm-PTH(1-34) | WVSEIQLMHNLGKHLNSMERVEWLRKKLQDVHNF-(PEG)₂-EYEK(palm)EYE-NH₂ |
| 4 | 2030 | W1-TMR-Palm-PTH(1-34) | WVSEIQLMHNLGK'HLNSMERVEWLRKKLQDVHNF-(PEG)₂-EYEK(palm)EYE-NH₂ |
| 5 | 2031 | Palm-Nle8, L11, dW12, W23-LA-PTH(7-36) | LNleHQLdWKWIQDARRRAWLHKLIAEIHTAEI-(PEG)₂-EYEK(palm)EYE-NH₂ |
| 5 | 2032 | Palm-Nle8, L11, dW12, K13TMR, W23-LA-PTH(7-36) | LNleHQLdWK'WIQDARRRAWLHKLIAEIHTAEI-(PEG)₂-EYEK(palm)EYE-NH₂ |
| 6 | 1844 | M-PTH(1-14) | AibVAibEIQLMHQHarAKW-NH₂ |
| 6 | 2090 | Palm-M-PTH(1-14) | AibVAibEIQLMHQHarAKW-(PEG)₂-EYEK(Palm)EYE-NH₂ |
| 7 | 2095 | Nle8, L11, dW12, W23, L25-LA-PTH(7-36) | LNleHQLdWKWIQDARRRAWLLKLIAEIHTAEI-NH₂ |
| 7 | 2089 | Palm-Nle8, L11, dW12, W23, L25-LA-PTH(7-36) | LNleHQdWKWIQDARRRAWLLKLIAEIHTAEI-(PEG)₂-EYEK(palm)EYE-NH₂ |
| 8 | — | Tag | EYEK(palm)EYE |

In Table 1, dW is dTrp, K' is Lys conjugated to tetramethylrhodamine (TMR), and (palm) is palmitoyl bonded to the nitrogen atom of the lysine sidechain. In Table 1, polypeptides of SEQ ID NOs: 5 and 7 are PTHR1 antagonists/inverse agonists, and the polypeptides of SEQ ID NOs: 1, 4, and 6 are PTHR1 agonists.

Preparation of Conjugates

Polypeptides

The polypeptides are amenable to production by solution- or solid-phase peptide synthesis and by in-situ synthesis using combination chemistry. The solid phase peptide synthesis technique, in particular, has been successfully applied in the production of human PTH and can be used for the production of these compounds (for guidance, see, e.g., Fairwell et al., Biochem. 22:2691, 1983). Success with Stewart and Young, "Solid Phase Peptide Synthesis," 2ⁿᵈ Edition, Pierce Chemical Company, Rockford, IL (1984).

Polypeptides of the invention can also be made recombinantly by any method known in the art. Prokaryotic (e.g., bacterial) and eukaryotic (e.g., yeast and mammalian) expression systems can also be used to produce polypeptides of the invention, particularly, where the polypeptide includes only proteinogenic amino acids.

Fatty Acid Acyl Conjugation

Conjugates of the invention may be prepared using techniques and reactions known in the art. For example, a fatty acid may be reacted with an unprotected —NH₂ in the lysine side-chain using amide coupling agents known in the art (e.g., dicyclohexylcarbodiimide and HOBt). The groups present in amino acids (e.g., —OH, —SH, —COOH, —NH$_2$, and the like) may be protected to avoid undesired reactions with the amide coupling agents and/or fatty acid. Commonly used protecting groups are known in the art, e.g., in Greene, "Protective Groups in Organic Synthesis," 3$^{rd}$ Edition (John Wiley & Sons, New York, 1999).

Polypeptide Modifications

Polypeptides of the invention may be modified (e.g., at the N-terminus). The polypeptides of the invention typically include amino acids with side chains amenable to modification, for example, through ester or thioester formation (e.g., Ser, Thr, Tyr, Glu, and Asp), amide formation (e.g., Lys, Glu, and Asp), ether formation (e.g., Ser, Thr, Cys), or amine formation (e.g., Lys). For example, the polypeptides of the invention can be modified to include, e.g., a dye (e.g., tetramethylrhodamine (TMR)). The inclusion of a dye can permit tracking the polypeptide of the invention in cells or in vivo through the use of fluorescence.

The polypeptides of the invention can include the dTrp12 modification (e.g., in the peptides lacking at least first four N-terminal amino acid residues). The dTrp12-modified, N-terminally truncated polypeptides of the invention typically have antagonist activity, and, in addition to their antagonist activity, can also function as PTHR1 inverse agonists.

Pharmaceutical Compositions

The conjugates disclosed herein may be formulated in a pharmaceutical composition providing an effective amount of the PTHR1 antagonist or inverse agonist to a subject upon administration. The pharmaceutical compositions of the conjugates disclosed herein can contain an appropriate amount of a suitable carrier or excipient. The pharmaceutical compositions may contain from 0.1% to 95% (w/v) or (w/w) of the PTHR1 antagonist or inverse agonist. The compositions may be provided in a dosage form that is suitable for parenteral (e.g., subcutaneous, intravenous, intramuscular, intraperitoneal), intranasal, transpulmonary, transdermal, transmucosal, or oral administration. Thus, the composition may be in the form of, e.g., tablets, ampules, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 21$^{st}$ edition, 2005, Ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York).

Pharmaceutical compositions may be formulated to release the active compound immediately upon administration or at a predetermined time or time period after administration. The latter types of compositions are generally known as controlled release formulations, which include (i) formulations that create substantially constant concentrations of the conjugates disclosed herein within the body over an extended period of time; (ii) formulations that after a predetermined lag time create substantially constant concentrations of the conjugates disclosed herein within the body over an extended period of time; (iii) formulations that sustain the action of the conjugates disclosed herein during a predetermined time period by maintaining a relatively constant, effective level of the conjugates disclosed herein in the body with concomitant minimization of undesirable side effects associated with fluctuations in the plasma level of the conjugates disclosed herein (sawtooth kinetic pattern); (iv) formulations that localize action of the conjugates disclosed herein, e.g., spatial placement of a controlled release composition adjacent to or in the diseased tissue or organ; (v) formulations that achieve convenience of dosing, e.g., administering the composition once per week or once every two weeks; and (vi) formulations that target the action of the conjugates disclosed herein by using carriers or chemical derivatives to deliver the compound to a particular target cell type. Administration of the compound in the form of a controlled release formulation is especially preferred for compounds having a narrow absorption window in the gastro-intestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, molecular complexes, microspheres, nanoparticles, patches, and liposomes.

The composition containing conjugates described herein may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), in vials containing several doses and in which a suitable preservative may be added, or in prefilled syringes. The composition may be in the form of a solution, a suspension, an emulsion, an infusion device, or a delivery device for implantation, or it may be presented as a dry powder to be reconstituted with water or another suitable vehicle before use. In addition to the conjugates disclosed herein, the composition may include suitable parenterally acceptable carriers and/or excipients. The conjugates disclosed herein may be incorporated into microspheres, microcapsules, nanoparticles, or liposomes for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable the conjugates disclosed herein are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Methods of Treatment

The conjugates and the pharmaceutical compositions disclosed herein may be used to treat a condition or a disease associated with PTHR1 signaling overactivity (e.g., hypercalcemia, hypophosphatemia, hyperparathyroidism, and Jansen's chondrodysplasia). PTHR1 signaling overactivity may be caused by various factors, such as elevated blood levels of PTH (e.g., hyperparathyroidism) or PTHrP (e.g., humoral hypercalcemia of malignancy).

Some forms of hypercalcemia are related to the interaction of PTHR1 with PTH or PTHrP (e.g., humoral hypercalcemia of malignancy). Hypercalcemia is a condition in which there is an abnormal elevation in serum calcium levels; it is often associated with other diseases, including hyperparathyroidism, osteoporosis, and cancer (e.g., carcinomas of the breast, lung and prostate, epidermoid cancers of the head and neck and of the esophagus, multiple myeloma, and hypernephroma).

Jansen's chondrodysplasia is a rare disease caused by PTHR1 activating mutations (e.g. H223R and T410P) which result in excessive hormone-independent (constitutive) signaling by the receptor itself. Ligands that bind to such constitutively active PTHR1 mutants and suppress their signaling are classified as PTHR1 inverse agonists. Some, but not all, ligands that function as PTHR1 antagonists also function as PTHR1 inverse agonists. Typically, among the conjugates disclosed herein, those including a dTrp12 modification function as inverse agonists.

In accordance with yet a further aspect of the invention, there is provided a method for treating a disease or condition that is caused by overactivity of PTHR1 in a subject. The method involves administering to the subject an effective amount of the conjugate of the invention or a pharmaceutically acceptable salt thereof or a fragment thereof or a pharmaceutical composition disclosed herein. The effective amount will typically be sufficient to reduce activation of the PTHR1 of the subject to non-pathological levels, as assessed by the treatment of the subject (e.g., a reduction in disease symptoms, reduced serum calcium levels).

In one embodiment, a subject having a disease or condition that is caused by the constitutive signaling activity of PTHR1 (e.g., Jansen's chondrodysplasia) can be treated using conjugates of the invention which are PTHR1 inverse agonists. In this embodiment, the PTHR1 inverse agonist conjugate of the invention may be present as a pharmaceutically acceptable salt thereof or a fragment thereof or in a pharmaceutical composition disclosed herein.

In another embodiment, a subject having a disease or condition that is caused by the non-constitutive signaling overactivity of PTHR1 can be treated using conjugates of the invention which are PTHR1 antagonists. In this embodiment, the PTHR1 antagonist conjugate of the invention may be present as a pharmaceutically acceptable salt thereof or a fragment thereof or in a pharmaceutical composition disclosed herein.

The conjugates and the pharmaceutical compositions disclosed herein may be used to treat a condition or a disease associated with PTHR1 signaling underactivity (e.g., hypoparathyroidism, hypocalcemia, hyperphosphatemia, osteoporosis, fracture repair, osteomalacia, arthritis (e.g., rheumatoid arthritis), or thrombocytopenia) or to increase stem cell mobilization in a subject. The conjugates and the pharmaceutical compositions disclosed herein may also be used to increase bone formation and activate bone remodeling, which may lead to an increase in bone mineral density.

PTHR1 signaling underactivity may be caused by reduced production of PTH from the parathyroid glands (e.g., hypoparathyroidism).

In accordance with yet a further aspect of the invention, there is provided a method for treating a disease or condition that is caused by underactivity of PTHR1 in a subject. The method involves administering to the subject an effective amount of the conjugate of the invention or a pharmaceutically acceptable salt thereof or a fragment thereof or a pharmaceutical composition disclosed herein. The effective amount will typically be sufficient to increase activation of the PTHR1 of the subject to non-pathological levels, as assessed by the treatment of the subject (e.g., a reduction in disease symptoms (paresthesia, muscle aches or cramps, muscle spasms, fatigue or weakness), increased bone formation or bone mineral density, increased calcium levels, reduced phosphate levels).

In one embodiment, a subject having a disease or condition that is caused by the reduced signaling activity of PTHR1 (e.g., hypoparathyroidism) can be treated using conjugates of the invention which are PTHR1 agonists. In this embodiment, the PTHR1 agonist conjugate of the invention may be present as a pharmaceutically acceptable salt thereof or a fragment thereof or in a pharmaceutical composition disclosed herein.

To administer the conjugate of the invention, the appropriate conjugate of the invention or a pharmaceutically acceptable salt thereof or a fragment thereof can be used in the manufacture of a medicament, generally by being formulated in an appropriate carrier or excipient such as, e.g., physiological saline, and administered through an appropriate route of administration (e.g., parenteral (e.g., subcutaneous, intravenous, intramuscular, intraperitoneal), intranasal, transpulmonary, transdermal, transmucosal, or oral administration). An effective amount of the conjugate of the invention is typically present in the medicament. For example, typical dosage would be 1 ng to 10 mg of the conjugate, e.g., per kg body weight, e.g., per day. In some embodiments, a subject may be administered a conjugate of the invention once daily or once every other day.

Methods of Modulating PTHR1 Activity

The conjugates disclosed herein may be used to modulate the activity of PTHR1 in a cell. Thus, the present invention features a method of inversely agonizing the activity of PTHR1 in a cell, a method of antagonizing the activity of PTHR1 in a cell, and a method of agonizing the activity of PTHR1 in a cell. The method may involve contacting the cell with a conjugate having a desirable activity (e.g., PTHR1 antagonist activity, PTHR1 inverse agonist activity, or PTHR1 agonist activity). The conjugate that is a PTHR1 antagonist may be used in this method to antagonize the signaling activity of PTHR1 in a cell (e.g., by reducing the binding of endogenous agonists to PTHR1). The conjugate that is a PTHR1 inverse agonist may be used in this method to inversely agonize the constitutive signaling activity of a naturally occurring PTHR1 mutant having constitutive signaling activity (e.g., PTHR1-H223R or PTHR1-T410P). A conjugate that is a PTHR1 antagonist or inverse agonist (e.g., in the case of PTHR1 mutants having constitutive signaling activity) may reduce receptor activity by 10%, 20%, 30%, 40%, 50%, 60%, 70%, 80%, 90%, 95%, 98% or more. The conjugate that is a PTHR1 agonist may be used in this method to agonize PTHR1 in a cell (e.g., by binding to PTHR1 and inducing or increasing PTHR1 signaling). A conjugate that is a PTHR1 agonist may increase PTHR1 activity by 10%, 20%, 30%, 40%, 50%, 60%, 70%, 80%, 90%, 95%, 98% or more. The cell may be in a mammal (e.g., in a subject).

It will be appreciated to those skilled in the art that the invention can be performed within a wide range of equivalent parameters of composition, concentration, modes of administration, and conditions without departing from the spirit or scope of the invention or any embodiment thereof. The following examples are meant to illustrate the invention. They are not meant to limit the invention in any way.

EXAMPLES

Example 1. Generation of PTH Analogs

Peptides and Synthesis

PTH peptides were based on the human PTH(1-34) sequence and were synthesized by the Massachusetts General Hospital Biopolymer Core facility using solid-phase chemistry. $Lys^{13}$(TMR) derivatives were obtained by post-synthetically attaching a fluorescent tetramethylrhodamine (TMR) group to the epsilon amino function of Lys-13. Sequences of the peptides are provided in Table 1. Palmitoyl tags were conjugated to the peptides using general techniques described by Zorzi et al., Nature Communications 10:1038/ncomms16092, 2017.

cAMP Signaling Properties of the Polypeptides in Cells cAMP signaling was assessed in an SaOS2-derived cell line stably expressing the luciferase-based GloSensor™ cAMP reporter (Hattersley et al., Paper presented at: Novel Signaling Mechanisms and Bone Cell Biology 2014; Binkowski et al., Methods in Molecular Biology 756:263-271, 2011). The cells were seeded into 96-well white plates and were assayed 24 to 48 hours post-confluency. Assays were performed at room temperature in $CO_2$-independent culture media (Life Technologies, Corp., Carlsbad, CA) containing 0.1% BSA (CIDB). The cells were pre-loaded with luciferin (0.5 mM in CIDB) for 15 minutes, then PTH peptides were added at varying concentrations. cAMP-dependent luminescence was measured at two-minute intervals using a PerkinElmer Envision plate reader. The time at which maximum luminescence (cps) observed with agonist alone, typically at 10-20 minutes after agonist addition, was used to obtain data from wells containing antagonist with or without agonist, to thus generate antagonist ligand dose-response curves. The resulting cps values were then plotted against ligand concentration using GraphPad Prism 7.0 software and a four-parameter logistics curve fitting equation, which yielded parameters of inhibitory potency ($pIC_{50}$).

In Vivo Testing of the Polypeptides Wild-type, ca. 10-week old male C57BL/6J mice were purchased from the Charles River Laboratories (Wilmington, Massachusetts, USA). The origin and method of breeding of Col1-H223R "Jansen's" transgenic mice is described by Calvi et al. (J. Clin. Invest. 107:277-286, 2001). Mice were maintained in facilities operated by the Center for Comparative Research of the Massachusetts General Hospital, and acclimated in the facilities for seven days prior to being used for study. All experimental procedures were approved by the MGH Institutional Animal Care and Use Committee (IACUC). In each study, animals were assigned randomly to treatment groups. Where possible, power calculations established that the number of animals used per study group was sufficient to detect statistically significant differences in intended primary experimental outcomes (i.e., changes in serum Ca and Pi).

Mice were injected IV via the tail vein or subcutaneously with ligands in vehicle (0.05% Tween 80; 10 mM citrate; 150 mM NaCl; pH 5.0) to give the intended final ligand dose (e.g. 50 nmol/kg body weight). At times immediately before (t=0) and after injection, tail vein blood was collected and analyzed for concentrations of administered peptides or blood ionized calcium ($Ca^{2+}$) measured with a RAPIDLAB 348 analyzer (SIEMENS Healthcare Diagnostic, United Kingdom).

Data Analysis

Data were processed using Microsoft Excel® and Graph-Pad Prism 7.0 software packages and analyzed statistically using Student's t test (two-tailed and unequal variances).

Results

Exemplary conjugates of the invention (see compounds 2027, 2028, 2029, 2030, 2031, and 2032 of Table 1) were made, and their properties were assessed in cells and in mice. We inserted a short linker $(PEG)_2$ (—C(O)—$CH_2$ $(OCH_2CH_2)_2CH_2CH_2$—NH—) between the C-terminal Phe (F) residue of PTH and the N-terminal Glu (E) residue of the tag.

The designed PTH analog maintained high potency on the PTH receptor in human osteoblast-derived SaOS-2 cells (FIG. 1; Table 2). In particular, palm-PTH(1-34) stimulated cAMP formation with nearly the same potency and efficacy as PTH(1-34) (EC50=~0.6 vs. 0.3 nM).

Figure 2:
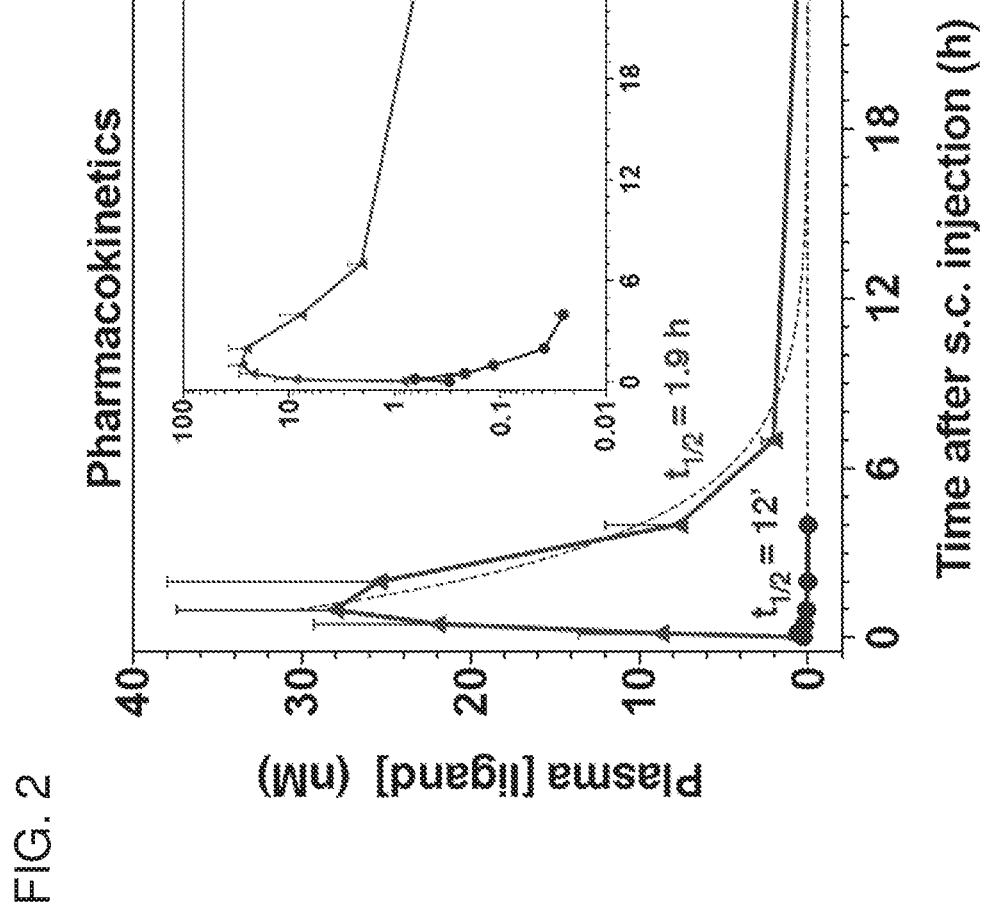
FIG. 2 is a graph showing pharmacokinetic properties of Palm-PTH(1-34) and PTH(1-34) in mice. Concentrations of the peptides were measured in mouse plasma immediately prior to injection (t=0) and at times after injection (peptide dose=10 nmol/kg, s.c.); concentrations measured by hPTH (1-34) ELISA kit (Immutopics Inc., Cat #60-3900) calibrated with each respective peptide; inset is log-scale y axis. Data are means±SEM; n=5 mice per group (exp.11/23/17.H.N.). Fit parameters are reported in Table 3.

Palm-PTH also exhibited markedly prolonged pharmacokinetic (PK) properties when injected into mice, as compared to conventional PTH(1-34) (FIG. 2). In particular, when a single dose was injected into mice, conjugate palm-PTH(1-34) (10 nmol/kg, intravenous (i.v.)) increased blood $Ca^{2+}$ levels for at least 24 hours, whereas an equal dose of PTH(1-34) increased blood $Ca^{2+}$ for no longer than 4 hours (FIG. 2). Fit parameters are reported in Table 3.

Figure 3:
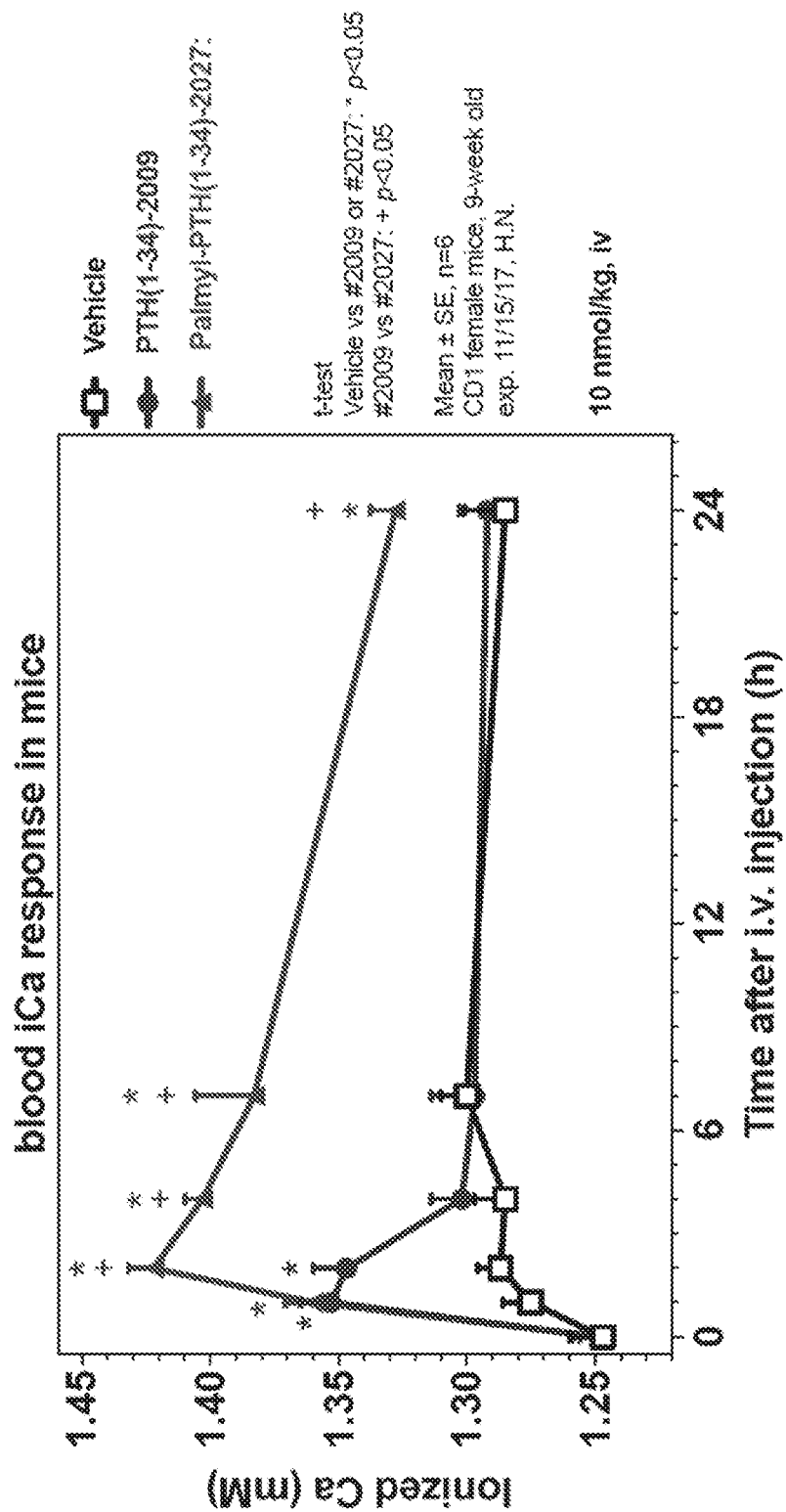
FIG. 3 is a graph showing concentrations of blood ionized calcium immediately prior to injection (t=0) and at times after injection with vehicle, Palm-PTH(1-34) or PTH(1-34) (peptide dose=10 nmol/kg, i.v.). Data are means±SEM; n=6 mice per group.

Conjugate palm-PTH(1-34) further induced prolonged hypophosphatemic effects, as compared to PTH(1-34). Consistent with these prolonged pharmacodynamics (PD) actions and the peptide design, palm-PTH(1-34) exhibited a markedly prolonged pharmacokinetic (PK) profile, as it was detected in the plasma (via a PTH(1-34) ELISA; Immutopics Inc.) for longer times than was PTH(1-34) (t½=1.9 vs. 0.2 h) after subcutaneous injection, and it attained a significantly greater total area-under-the-curve (116 nanomole-h/L vs. 0.43 nanomole-h/L) following a single injection (10 mnol/kg, subcutaneous (s.c.)) (FIG. 3).

The findings indicate that conjugates of the invention (e.g., palm-PTH(1-34)) can effectively bind to and activate the PTH-1 receptor in target cells, while having superior pharmacokinetic properties. In addition to this palm-PTH (1-34), we have developed other conjugates including PTHR1 binders designed to function as long-acting antagonists, inverse agonists, or signal-selective biased-agonists (see Table 1).

TABLE 2 cAMP signaling potency in SaOS2/glosensor (SGS-72) cells

| | $pEC_{50}$* | | Max % | |
|---|---|---|---|---|
| PTH(1-34)-2009 | 9.79 ± 0.03 0.162 | P | 100 ± 0 | P |
| Palm-PTH(1-34)-2027 | 9.81 ± 0.09 0.155 | 0.8 | 85 ± 1 | 0.0020 |
| Trp1-Palm-PTH(1-34)-2029 | 8.72 ± 0.15 1.905 | 0.0050 | 77 ± 8 | 0.1 |

*log molar concentration to attain 50% of maximum response observed with PTH(1-34)-2009; concentration in nM shown below. Means ± SEM; n = 5, experiments; P = t test vs. PTH(1-34).

TABLE 3

| Pharmacokinetic properties in mice | | | | |
|---|---|---|---|---|
| | t½ (hours)* | AUC | Cmax | Tmax |
| PTH(1-34)-2009 | 0.2 | 0.43 | 0.65 | 0.17 |
| Palm-PTH(1-34)-2027 | 1.9 | 116 | 28.1 | 1.0 |

Ligand concentrations in mouse blood after s.c. injection of peptide (10 nmol/kg) were measured by hPTH(1-34) ELISA (Immutopics Inc.) and means (5 mice per group) were plotted vs. time and analyzed for t½ (monophasic decay), area-under the curve (AUC), peak concentration (Cmax), and time of Cmax (Tmax).

Figure 4A:
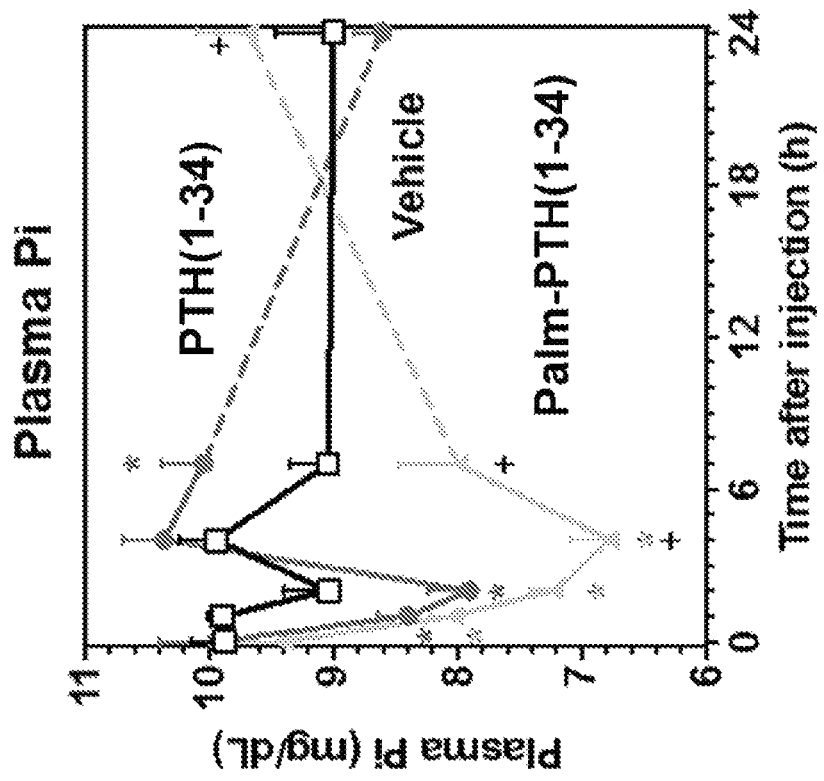
FIGS. 4A, 4B, 4C, and 4D are graphs showing levels of ionized calcium (FIG. 4A), total inorganic phosphorus (FIGS. 4B and 4D), and total calcium (FIG. 4C) in mice after injection with vehicle, PTH(1-34) (#2009), or Palm-PTH(1-34) (#2027). Tail vein blood and spot urine were collected just prior to injection (t=0) and at the indicated times after injection.
Figure 4B:
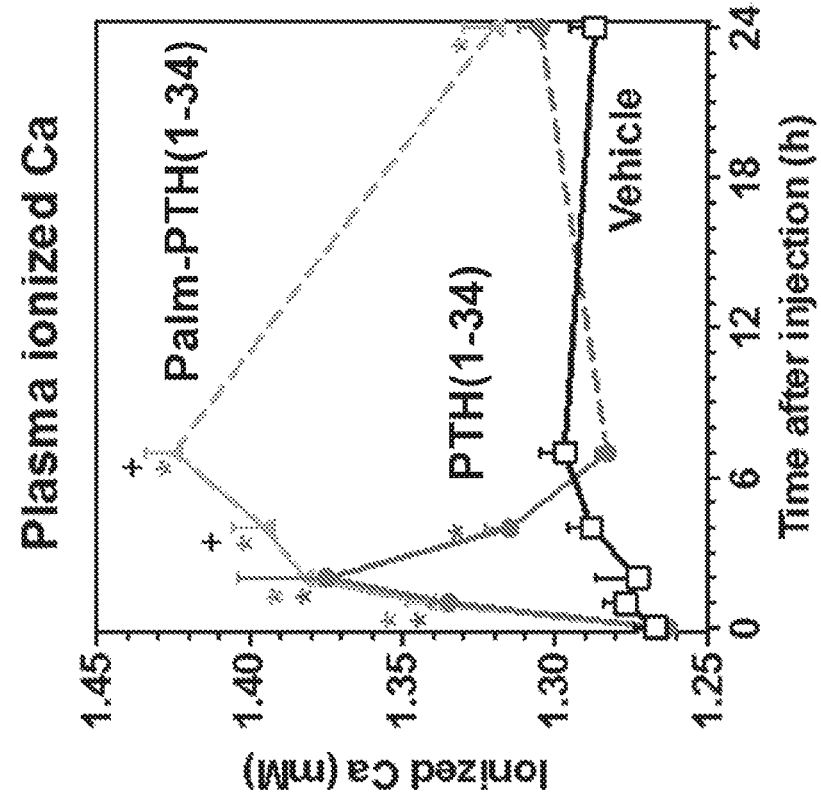
Figure 4D:
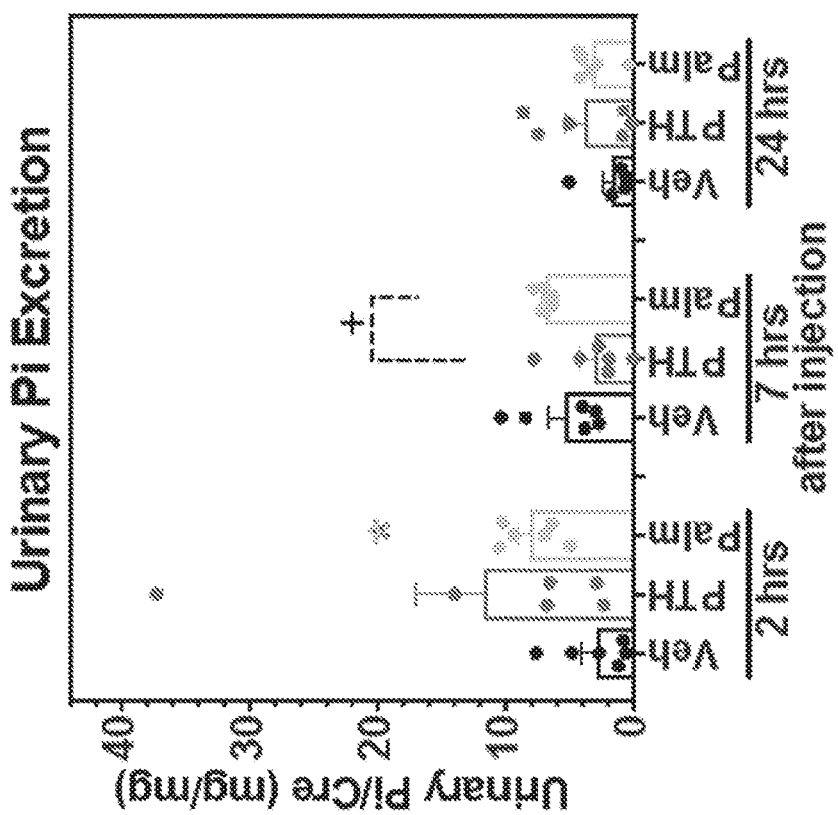
Figure 4C:
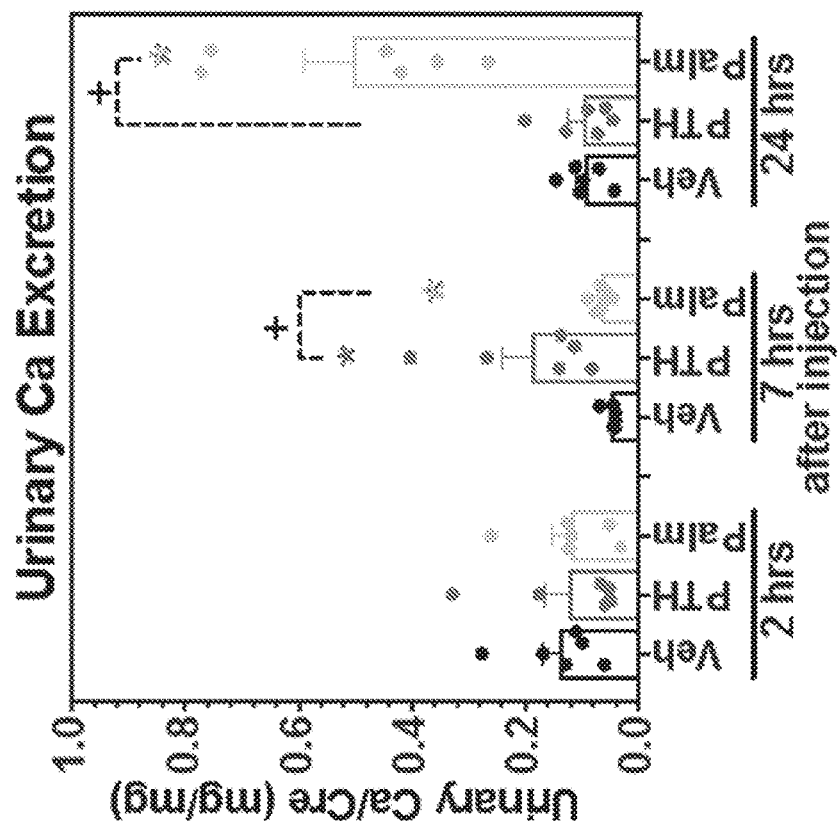

Example 2. Palmitoylation Enhances Calcemic and Phosphaturic Activity of PTH(1-34) in Mice Mice were injected s.c. with vehicle, PTH(1-34) (#2009), or Palm-PTH(1-34) (#2027) and tail vein blood and spot urine were collected at the indicated times after injection and just prior to injection (t=0) and measured for ionized calcium (FIG. 4A), total calcium (FIG. 4C), and total inorganic phosphorus (Pi) (FIGS. 4B and 4D). Peptide doses for FIGS. 4A and 4B were 10 nmol/kg, while peptide doses were 50 nmol/kg for FIGS. 4C and 4D. T-test vs. vehicle: *$p<0.05$; PTH vs. Palm: +$p<0.05$. Mice were CD1 females, age 10 weeks. Data are means±SEM, n=6.

Figure 5:
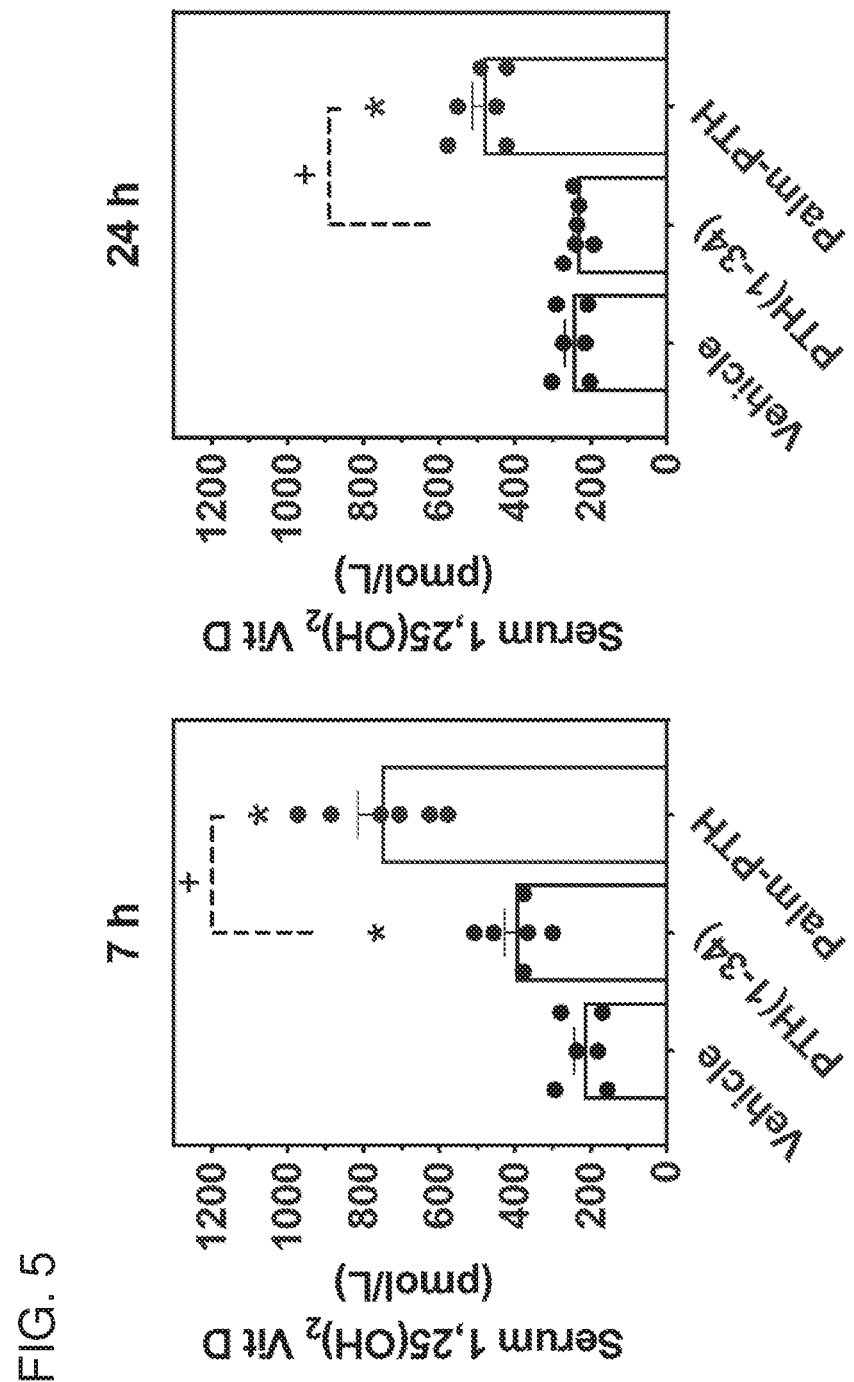
FIG. 5 is a series of graphs showing serum levels of 1,25(OH)$_2$-vitamin D in mice after injection with vehicle, PTH(1-34) (#2009), or Palm-PTH(1-34) (#2027) at peptide doses of 50 nmol/kg. Tail vein blood was collected at 7 hr and 24 hr after injection and measured by EIA for 1,25 (OH)$_2$-vitamin D.

Example 3. Palmitoylation Enhances PTH(1-34)-Induced Stimulation of 1,25(OH)$_2$-Vitamin D Synthesis in Normal Mice Intact mice were injected s.c. with vehicle, PTH(1-34) (#2009), or Palm-PTH(1-34) (#2027). Palm-PTH(1-34) was administered at peptide doses of 50 nmol/kg and tail vein blood was collected at 7 hr and 24 hr after injection and measured by enzyme immunoassay (EIA) for 1,25(OH)$_2$-vitamin D. Data are shown in FIG. 5. T-test vs. vehicle: *$p<0.05$; PTH(1-34) vs. Palm-PTH: +$p<0.05$. Mice were CD1 females, age 9 weeks. Data are means±SEM, n=6.

Figure 6B:
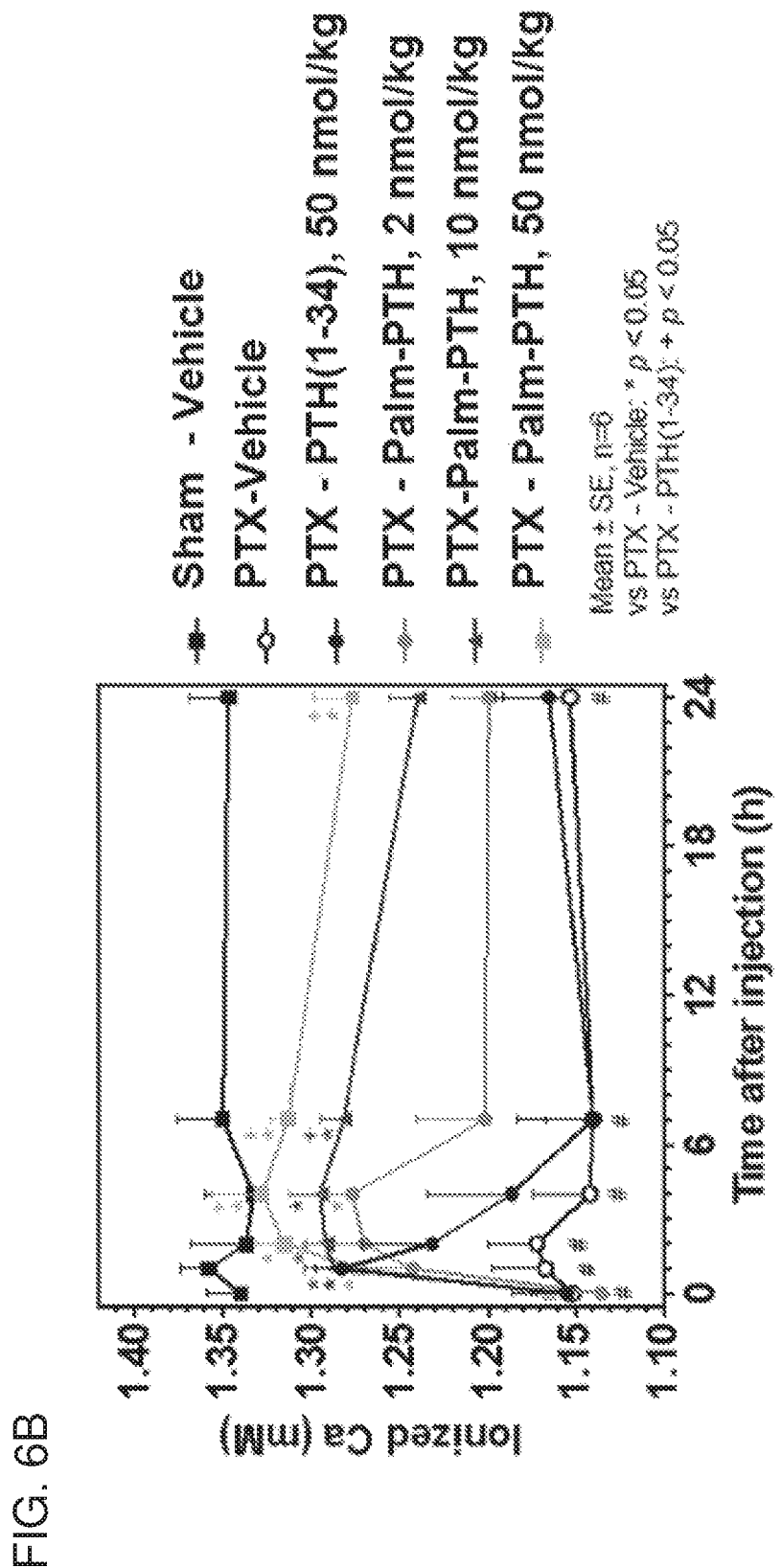
Figure 6C:
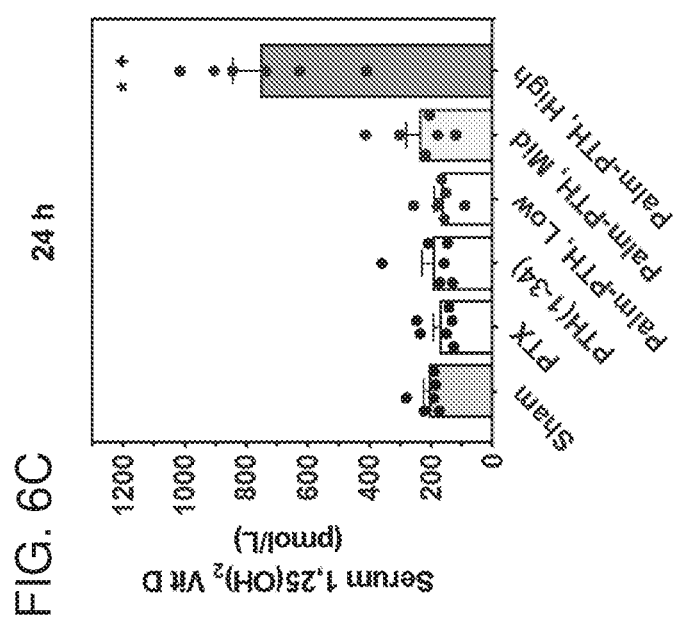

Example 4. Palmitoylation Enhances PTH(1-34)-Induced Calcemic Effect and Stimulation of 1,25(OH)$_2$-Vitamin D Synthesis in Parathyroidectimized (PTX) Mice Surgical parathyroidectomy (PTX) or sham surgery was performed on PTH-Cre; Rosa$^{mT/mG}$ mice (Bi et al., J. Bone Miner. Res. 31(5):975-84, 2016), and four days after surgery, when blood Ca$^{2+}$ in PTX mice was low (FIG. 6A), the mice were injected s.c. with vehicle, PTH(1-34) (#2009), or Palm-PTH(1-34) (#2027) at the peptide doses indicated. Blood samples were collected at the times displayed (t=0 is just prior to injection) and measured for ionized calcium (iCa$^{2+}$) using a Siemens RapidLab 348 Ca$^{2+}$/pH analyzer (FIG. 6B). Levels of 1,25(OH)$_2$-vitamin D in serum collected from the mice at 24 hours were measured by EIA. T-test vs. vehicle: *$p<0.05$; PTH vs. Palm-PTH(1-34): +$p<0.05$. Mice were CD1 females, age 10 weeks. Data are means±SEM, n=6.

Example 5. Palmitoylation Reduces Renal Filtration of PTH(1-34) in Normal Mice

Figure 7:
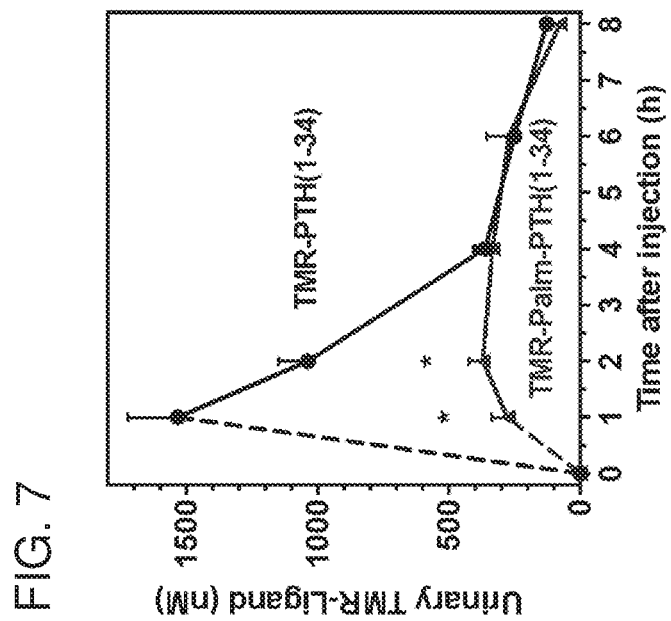
FIG. 7 is a graph showing TMR-PTH(1-34) (#2010) and TMR-Palm-PTH(1-34) (#2028) levels in mice measured by TMR fluorescence. Urine was collected just prior to injection (t=0) and at the indicated times after injection.

Mice were injected with TMR-labeled PTH(1-34) (TMR-PTH(1-34), #2010) or TMR-labeled Palm-PTH(1-34) (TMR-Palm-PTH(1-34), #2028) at peptide doses of 50 nmol/kg. Urine was collected at the indicated times after injection (t=0 is just prior to injection) and measured for TMR fluorescence (λexc.=510 nm; λexc.=580 nm) using a PerkinElmer Envision plate reader. The measured values of TMR fluorescence were converted to peptide concentration (nM in the urine) by interpolation from a standard curve generated using serial dilutions of the corresponding stock TMR-labeled peptide ligand (FIG. 7). T-test *$p<0.05$; PTH vs. Palm-PTH(1-34). Mice were CD1 females, age 10 weeks. Data are means±SEM, n=6.

Figure 8:
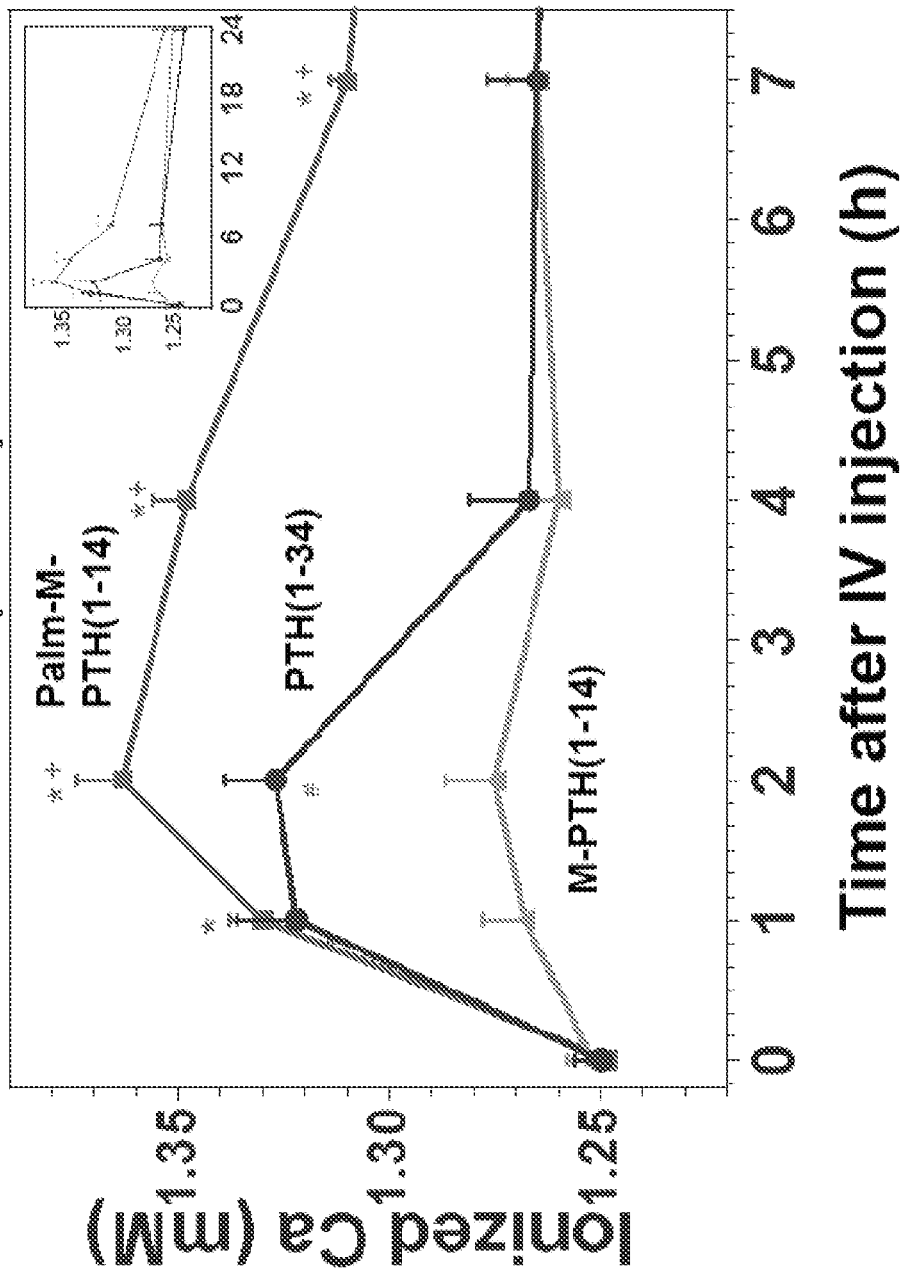
FIG. 8 is a graph showing levels of ionized calcium in mice after injection with PTH(1-34) (#2009), M-PTH(1-14) (#1844), or Palm-M-PTH(1-14) (#2090) at peptide doses of 10 nmol/kg. Tail vein blood was collected just prior to injection (t=0) and at the indicated times after injection.

Example 6. Palmitoylation Enhances Activity of a Minimized M-PTH(1-14) Analog in Normal Mice Mice were injected i.v. with PTH(1-34) (#2009), M-PTH (1-14) (#1844) or palmitoyl-M-PTH (Palm-M-PTH(1-14), #2090). Tail vein blood was collected at the indicated times after injection and just prior to injection (t=0) and measured for ionized calcium (FIG. 8). Peptide doses were 10 nmol/kg. T-test vs Vehicle: *$p<0.05$; PTH vs. Palm: +$p<0.05$. Mice were CD1 females, age 9 weeks. Data are means±SEM, n=6; Inset shows the same data set with the 24 hour time point included.

Figure 9:
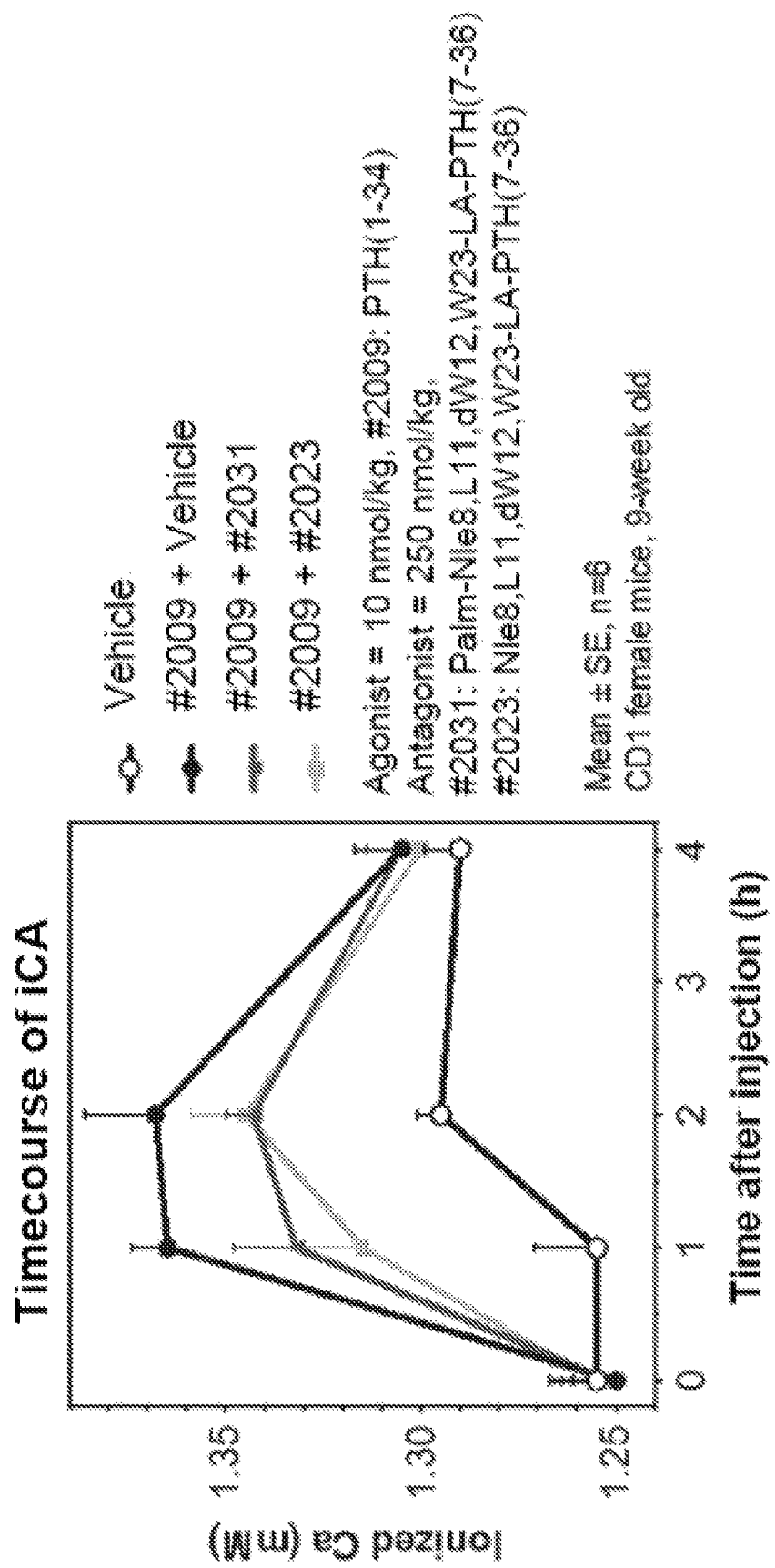
FIG. 9 is a graph showing levels of ionized calcium after injection with vehicle, PTH(1-34) (#2009) alone, or PTH (1-34) with either Palm-LA-PTH(7-36) (#2031) or LA-PTH (7-36) (#2023) at peptide doses of 10 nmol/kg for PTH(1-34) and 250 nmol/kg for PTH(7-36) analogs. Tail vein blood was collected at the indicated times just prior to injection (t=0) and after at the indicated times after injection.

Example 7. Palmitoylation Preserve Antagonist Action of a PTH(7-36) Peptide in Mice Intact mice were injected i.v. with vehicle, PTH(1-34) (#2009) alone, or with PTH(1-34) plus either Palm-LA-PTH (7-36) (#2031) or LA-PTH(7-36) (#2023) at peptide doses of 10 nmol/kg for PTH(1-34) and 250 nmol/kg for PTH(7-36) analogs. Tail vein blood was collected at the indicated times after injection and just prior to injection (t=0) and measured for ionized calcium (FIG. 9). Mice were CD1 females, age 9 weeks. Data are means±SEM, n=6.

Some embodiments of the technology described herein can be defined according to any one of the following numbered paragraphs:

1. A conjugate, or a pharmaceutically acceptable salt thereof, comprising a fatty acid acyl covalently linked to a PTHR1 agonist, PTHR1 antagonist, or PTHR1 inverse agonist peptide or a fragment thereof comprising 14 to 37 contiguous amino acid residues.
2. The conjugate of paragraph 1, wherein the fragment comprises 24 to 37 contiguous amino acid residues.
3. A conjugate, or a pharmaceutically acceptable salt thereof, comprising a polypeptide and a fatty acid acyl covalently linked to the polypeptide, wherein the polypeptide comprises a sequence of formula (I):

(I)
(SEQ ID NO: 9)
$X_{01}$-$X_{02}$-$X_{03}$-$X_{04}$-$X_{05}$-$X_{06}$-Leu-$X_{08}$-His-$X_{10}$-$X_{11}$-$X_{12}$-$X_{13}$-$X_{14}$-$X_{15}$-$X_{16}$-$X_{17}$-$X_{18}$-$X_{19}$-Arg-$X_{21}$-$X_{22}$-$X_{23}$-Leu-$X_{25}$-$X_{26}$-$X_{27}$-$X_{28}$-$X_{29}$-$X_{30}$-$X_{31}$-His-$X_{33}$-$X_{34}$-$X_{35}$-$X_{36}$-$X_{37}$, wherein
$X_{01}$ is Ser, Trp, Ala, Aib, or absent;
$X_{02}$ is Val or absent;
$X_{03}$ is Ser, Ala, Aib, or absent;
$X_{04}$ is Glu or absent;
$X_{05}$ is Ile, His, or absent;
$X_{06}$ is Gln, or absent;
$X_{08}$ is Met, Leu, or Nle;
$X_{10}$ is Asn, Ala, Val, Asp, Glu, or Gln;
$X_{11}$ is Leu, Ala, Val, Met, Lys, Ile, Arg, Har, or Trp;

$X_{12}$ is Gly, Ala, His, Arg, or dTrp;
$X_{13}$ is Lys, Ala, Leu, Gln, Arg, His, or Trp;
$X_{14}$ is His, Leu, Arg, Phe, Trp, or Ser;
$X_{15}$ is Leu or Ile;
$X_{16}$ is Asn or Gln;
$X_{17}$ is Ser or Asp;
$X_{18}$ is Met, Ala, Leu, Glu, Ser, or Phe;
$X_{19}$ is Glu or Arg;
$X_{21}$ is Val or Arg;
$X_{22}$ is Glu, Ala, Phe, Ser, Leu, Asn, Trp, or Lys;
$X_{23}$ is Trp, Phe, or Leu;
$X_{25}$ is Arg, His, Leu, Glu, Trp, or Lys;
$X_{26}$ is Lys, His, Ala, Ser, Asn, or Arg;
$X_{27}$ is Lys or Leu;
$X_{28}$ is Leu or Ile;
$X_{29}$ is Gln, Ala, Aib, or absent;
$X_{30}$ is Asp, Glu, Lys, or absent;
$X_{31}$ is Val, Leu, Ile, or absent;
$X_{33}$ is Asn, Thr, or absent;
$X_{34}$ is Phe, Ala, or absent;
$X_{35}$ is absent or Glu;
$X_{36}$ is absent or Ile; and
$X_{37}$ is absent or Cys,
or a fragment thereof comprising 14 to 30 contiguous amino acid residues.

4. The conjugate of paragraph 3, wherein the fragment comprises 24 to 30 contiguous amino acid residues.

5. The conjugate of paragraph 3 or 4, wherein $X_{29}$-$X_{34}$ are not absent.

6. The conjugate of any one of paragraphs 3 to 5, wherein $X_{37}$ is absent.

7. The conjugate of any one of paragraphs 1 to 6, further comprising an additional modification.

8. The conjugate of paragraph 7, wherein the modification is a dye.

9. The conjugate of paragraph 8, wherein the dye is conjugated to a Lys residue in the peptide or polypeptide.

10. The conjugate of any one of paragraphs 1 to 9, wherein the fatty acid acyl is covalently linked to the C-terminus of the peptide or polypeptide.

11. The conjugate of any one of paragraphs 1 to 10, wherein the fatty acid acyl is covalently linked to the peptide or polypeptide through a linker of the structure:

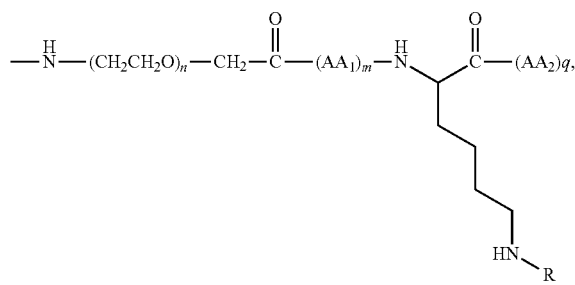

wherein
n is an integer from 0 to 10;
each of m and q is an integer from 2 to 5;
each $AA_1$ and each $AA_2$ is independently a proteinogenic amino acid; and
R is a bond to the carbonyl carbon of the fatty acid acyl.

12. The conjugate of paragraph 11, wherein —C(O)-$(AA_1)_m$-NH— in the linker structure is —C(O)-EYE-NH— or —C(O)—SYE-NH—.

13. The conjugate of paragraph 11 or 12, wherein -$(AA_2)_q$ in the linker structure is -EYE or -ESE.

14. The conjugate of any one of paragraphs 11 to 13, wherein the C-terminus of -$(AA_2)_q$ is carboxamide.

15. The conjugate of any one of paragraphs 1 to 14, wherein the fatty acid acyl is a very long chain fatty acid or a long chain fatty acid acyl.

16. The conjugate of paragraph 15, wherein the fatty acid acyl is a long chain fatty acid.

17. The conjugate of paragraph 16, wherein the long chain fatty acid acyl is palmitoyl.

18. The conjugate of any one of paragraphs 1 to 17, wherein the polypeptide comprises a sequence of formula (II):

(II)

(SEQ ID NO: 10)
$X_{05}$-$X_{06}$-Leu-$X_{08}$-His-$X_{10}$-$X_{11}$-$X_{12}$-$X_{13}$-$X_{14}$-$X_{15}$-$X_{16}$-$X_{17}$-$X_{18}$-Arg-Arg-Arg-$X_{22}$-$X_{23}$-Leu-$X_{25}$-$X_{26}$-Leu-Ile-Ala-Glu-Ile-His-Thr-Ala-Glu-Glu-$X_{36}$-$X_{37}$, wherein
$X_{05}$ is absent or Ile;
$X_{06}$ is absent or Gln;
$X_{08}$ is Met, Leu, or Nle;
$X_{10}$ is Asn, Ala, Val, Asp, Glu, or Gln;
$X_{11}$ is Leu, Ala, Val, Met, Lys, Ile, Arg, Har, or Trp;
$X_{12}$ is Gly, Ala, His, Arg, or dTrp;
$X_{13}$ is Lys, Ala, Leu, Gln, Arg, His, or Trp;
$X_{14}$ is His, Leu, Arg, Phe, Trp, or Ala;
$X_{15}$ is Ile or Leu;
$X_{16}$ is Gln or Asn;
$X_{17}$ is Asp or Ser;
$X_{18}$ is Ala, Leu, Met, Glu, Ser, or Phe;
$X_{22}$ is Ala, Phe, Glu, Ser, Leu, Asn, Trp, or Lys;
$X_{23}$ is Phe or Trp;
$X_{25}$ is His, Arg, Leu, Trp, or Lys;
$X_{26}$ is Lys, His, Ala, Ser, Asn, or Arg;
$X_{36}$ is Ile, Cys, or Tyr; and
$X_{37}$ is absent or Cys;
or a fragment thereof comprising from 24 to 30 contiguous amino acid residues.

19. The conjugate of paragraph 18, wherein the polypeptide is a fragment comprising amino acid residues 1-32 of formula (II).

20. The conjugate of paragraph 18, wherein the polypeptide is a fragment comprising amino acid residues 3-32 of formula (II).

21. The conjugate of paragraph 18, wherein the polypeptide is a fragment comprising amino acid residues 3-33 of formula (II).

22. The conjugate of any one of paragraphs 18 to 21, wherein $X_{08}$ is Met, $X_{12}$ is Ala, $X_{23}$ is Phe, and $X_{36}$ is Ile.

23. The conjugate of any one of paragraphs 18 to 21, wherein $X_{08}$ is Met, $X_{12}$ is dTrp, $X_{23}$ is Trp, and $X_{36}$ is Ile.

24. The conjugate of any one of paragraphs 18 to 21, wherein $X_{08}$ is Nle, $X_{12}$ is dTrp, $X_{23}$ is Trp, and $X_{36}$ is Tyr.

25. The conjugate of any one of paragraphs 18 to 21, wherein $X_{08}$ is Nle, $X_{12}$ is dTrp, $X_{23}$ is Trp, and $X_{36}$ is Cys.

26. The conjugate of any one of paragraphs 18 to 21, wherein $X_{08}$ is Nle, $X_{12}$ is dTrp, $X_{23}$ is Trp, and $X_{36}$ is Ile.

27. The conjugate of any one of paragraphs 18 to 21, wherein $X_{08}$ is Met, $X_{12}$ is dTrp, $X_{23}$ is Trp, and $X_{36}$ is Ile.
28. The conjugate of any one of paragraphs 18 to 21, wherein $X_{08}$ is Nle, $X_{11}$ is Leu, $X_{12}$ is dTrp, and $X_{23}$ is Trp.
29. The conjugate of any one of paragraphs 18 to 21, wherein $X_{08}$ is Nle, $X_{11}$ is Leu, $X_{12}$ is dTrp, $X_{13}$ is Lys, and $X_{23}$ is Trp.
30. The conjugate of paragraph 18, wherein the polypeptide has the amino acid sequence
Leu-Nle-His-Gln-Leu-dTrp-Lys-Trp-Ile-Gln-Asp-Ala-Arg-Arg-Arg-Ala-Trp-Leu-His-Lys-Leu-Ile-Ala-Glu-Ile-His-Thr-Ala-Glu-Ile (SEQ ID NO: 5); or
Leu-Nle-His-Gln-Leu-dTrp-Lys-Trp-Ile-Gln-Asp-Ala-Arg-Arg-Arg-Ala-Trp-Leu-Leu-Lys-Leu-Ile-Ala-Glu-Ile-His-Thr-Ala-Glu-Ile (SEQ ID NO: 7); or
a 3-32 or 3-33 fragment thereof.
31. The conjugate of any one of paragraphs 1 to 30, wherein the polypeptide is a PTH receptor antagonist or inverse agonist.
32. The conjugate of any one of paragraphs 1 to 17, wherein the polypeptide comprises a sequence of formula (III):

(III)
(SEQ ID NO: 11)
$X_{01}$-Val-$X_{03}$-Glu-$X_{05}$-Gln-Leu-$X_{08}$-His-$X_{10}$-$X_{11}$-$X_{12}$-$X_{13}$-$X_{14}$-$X_{15}$-$X_{16}$-$X_{17}$-$X_{18}$-$X_{19}$-Arg-$X_{21}$-$X_{22}$-$X_{23}$-Leu-$X_{25}$-$X_{26}$-$X_{27}$-$X_{28}$-$X_{29}$-$X_{30}$-$X_{31}$-$X_{32}$-$X_{33}$-$X_{34}$-$X_{35}$-$X_{36}$, wherein
$X_{01}$ is Ser, Ala, Trp, or Aib;
$X_{03}$ is Ser, Ala, or Aib;
$X_{05}$ is Ile or His;
$X_{08}$ is Met, Leu, or Nle;
$X_{10}$ is Asn, Ala, Val, Asp, Glu, or Gln;
$X_{11}$ is Leu, Ala, Val, Met, Lys, Ile, Arg, Har, or Trp;
$X_{12}$ is Gly, Ala, His, or Arg;
$X_{13}$ is Lys, Ala, Leu, Gln, Arg, His, or Trp;
$X_{14}$ is His, Leu, Arg, Phe, Trp, or Ser;
$X_{15}$ is Ile or Leu;
$X_{16}$ is Gln or Asn;
$X_{17}$ is Asp or Ser;
$X_{18}$ is Ala, Leu, Met, Glu, Ser, or Phe;
$X_{19}$ is Glu or Arg;
$X_{21}$ is Arg or Val;
$X_{22}$ is Ala, Phe, Glu, Ser, Leu, Asn, Trp, or Lys;
$X_{23}$ is Trp, Phe, or Leu;
$X_{25}$ is His, Arg, Leu, Glu, Trp, or Lys; and
$X_{26}$ is Lys, His, Ala, Ser, Asn, or Arg;
$X_{27}$ is Lys or Leu;
$X_{28}$ is Leu or Ile;
$X_{29}$ is absent, Gln, Aib, or Ala;
$X_{30}$ is absent, Asp, Lys, or Glu;
$X_{31}$ is absent, Val, Leu, or Ile;
$X_{32}$ is absent or His;
$X_{33}$ is absent, Asn, or Thr;
$X_{34}$ is absent, Phe, or Ala;
$X_{35}$ is absent or Glu; and
$X_{36}$ is absent or Ile;
or a fragment thereof comprising from 14 to 30 contiguous amino acid residues.
33. The conjugate of paragraph 32, wherein the fragment comprises 28 to 30 contiguous amino acid residues.
34. The conjugate of paragraph 32 or 33, wherein $X_{35}$ and $X_{36}$ are absent.

35. The conjugate of any one of paragraphs 32 to 34, wherein $X_{01}$ and $X_{03}$ are Ala; $X_{10}$ is Gln; $X_{11}$ is Arg; $X_{12}$ is Ala; and $X_{14}$ is Trp.
36. The conjugate of any one of paragraphs 32 to 34, wherein $X_{01}$ is Ala; $X_{03}$ is Aib; $X_{10}$ is Gln; $X_{11}$ is Har; $X_{12}$ is Ala; and $X_{14}$ is Trp.
37. The conjugate of any one of paragraphs 32 to 34, wherein $X_{01}$ is Trp.
38. The conjugate of any one of paragraphs 32 to 37, wherein $X_{18}$ is Ala; $X_{22}$ is Ala; or $X_{26}$ is Lys.
39. The conjugate of paragraph 38, wherein $X_{18}$ is Ala; $X_{22}$ is Ala; and $X_{26}$ is Lys.
40. The conjugate of paragraph 32, wherein the polypeptide has the amino acid sequence:

(SEQ ID NO: 1)
Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe;

(SEQ ID NO: 4)
Trp-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe;

(SEQ ID NO: 6)
Aib-Val-Aib-Glu-Ile-Gln-Leu-Met-His-Gln-Har-Ala-Lys-Trp;
or a fragment comprising from 14 to 30 contiguous amino acid residues of SEQ ID NO: 1 or SEQ ID NO: 4.
41. The conjugate of paragraph 1, wherein the polypeptide is hPTH(1-84) or a fragment thereof comprising 28 to 34 contiguous N-terminal amino acids.
42. The conjugate of any of one of paragraphs 1 to 17 and 32 to 41, wherein the polypeptide is a PTH receptor agonist.
43. A pharmaceutical composition comprising the conjugate of any one of paragraphs 1 to 31 and one or more pharmaceutically acceptable carriers or excipients.
44. A pharmaceutical composition comprising the conjugate of any one of paragraphs 1 to 17 and 32 to 42 and one or more pharmaceutically acceptable carriers or excipients.
45. A method of modulating the activity of parathyroid hormone receptor 1 (PTHR1) in a cell, the method comprising contacting the cell with the conjugate of any one of paragraphs 1 to 42 or the pharmaceutical composition of paragraph 43 or 44.
46. A method of antagonizing or inversely agonizing the activity of PTHR1 in a cell, the method comprising contacting the cell with the conjugate of any one of paragraphs 1 to 31 or the pharmaceutical composition of paragraph 43.
47. A method of agonizing the activity of PTHR1 in a cell, the method comprising contacting the cell with the conjugate of any one of paragraphs 1 to 17 and 32 to 42 or the pharmaceutical composition of paragraph 44.
48. The method of any one of paragraphs 45 to 47, wherein the cell is a human cell.
49. A method of treating a subject with a disease or condition associated with PTHR1 signaling overactivity, the method comprising administering to the subject an effective amount of the conjugate of any one of paragraphs 1 to 31 or the pharmaceutical composition of paragraph 43.

50. The method of paragraph 49, wherein the disease or condition is hypercalcemia, hypophosphatemia, hyperparathyroidism, or Jansen's chondrodysplasia.
51. The method of paragraph 49 or 50, wherein the conjugate or pharmaceutical composition is administered in an amount sufficient to reduce PTHR1 signaling.
52. A method of treating a subject having a disease selected from the group consisting of hypoparathyroidism, hyperphosphatemia, osteoporosis, fracture repair, osteomalacia, arthritis, thrombocytopenia, and chronic kidney disease, the method comprising administering to the subject the conjugate of any one paragraphs 1 to 17 and 31 to 42 or the pharmaceutical composition of paragraph 44 in an amount sufficient to treat said disease.
53. The method of any one of paragraphs 49 to 52, wherein the administering comprises subcutaneous, intravenous, intranasal, transpulmonary, transdermal, transmucosal, or oral administration of the conjugate or pharmaceutical composition to the subject.
54. The conjugate of any one of paragraphs 1 to 42, the pharmaceutical composition of paragraph 43 or 44, or the method of any one of paragraphs 45 to 53, wherein the polypeptide is fewer than 50 amino acids in length.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are within the scope of the claims.

What is claimed is:

1. A conjugate, or a pharmaceutically acceptable salt thereof, comprising a polypeptide and a fatty acid acyl covalently linked to the polypeptide, wherein the polypeptide comprises a sequence of formula (I):

(I)
(SEQ ID NO: 9)
$X_{01}$-$X_{02}$-$X_{03}$-$X_{04}$-$X_{05}$-$X_{06}$-Leu-$X_{08}$-His-$X_{10}$-$X_{11}$-$X_{12}$-$X_{13}$-$X_{14}$-$X_{15}$-$X_{16}$-$X_{17}$-$X_{18}$-$X_{19}$-Arg-$X_{21}$-$X_{22}$-$X_{23}$-Leu-$X_{25}$-$X_{26}$-$X_{27}$-$X_{28}$-$X_{29}$-$X_{30}$-$X_{31}$-His-$X_{33}$-$X_{34}$-$X_{35}$-$X_{36}$-$X_{37}$, wherein
$X_{01}$ is absent;
$X_{02}$ is absent;
$X_{03}$ is absent;
$X_{04}$ is absent;
$X_{05}$ is absent;
$X_{06}$ is absent;
$X_{08}$ is Nle;
$X_{10}$ is Asn, Ala, Val, Asp, Glu, or Gln;
$X_{11}$ is Leu, Ala, Val, Met, Lys, Ile, Arg, Har, or Trp;
$X_{12}$ is dTrp;
$X_{13}$ is Lys, Ala, Leu, Gln, Arg, His, or Trp;
$X_{14}$ is His, Leu, Arg, Phe, Trp, or Ser;
$X_{15}$ is Leu or Ile;
$X_{16}$ is Asn or Gln;
$X_{17}$ is Ser or Asp;
$X_{18}$ is Met, Ala, Leu, Glu, Ser, or Phe;
$X_{19}$ is Glu or Arg;
$X_{21}$ is Val or Arg;
$X_{22}$ is Glu, Ala, Phe, Ser, Leu, Asn, Trp, or Lys;
$X_{23}$ is Trp, Phe, or Leu;
$X_{25}$ is Arg, His, Leu, Glu, Trp, or Lys;
$X_{26}$ is Lys, His, Ala, Ser, Asn, or Arg;
$X_{27}$ is Lys or Leu;
$X_{28}$ is Leu or Ile;
$X_{29}$ is Gln, Ala, or Aib;
$X_{30}$ is Asp, Glu, or Lys;
$X_{31}$ is Val, Leu, or Ile;
$X_{33}$ is Asn or Thr;
$X_{34}$ is Phe or Ala;
$X_{35}$ is Glu;
$X_{36}$ is Ile; and
$X_{37}$ is absent, wherein the fatty acid acyl is covalently linked to the C-terminus of the polypeptide through a linker of the structure:

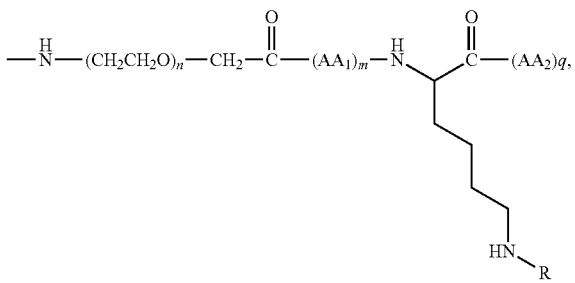

wherein
n is an integer from 0 to 10;
each of m and q is an integer from 2 to 5;
each $AA_1$ and each $AA_2$ is independently a proteinogenic amino acid; and
R is a bond to the carbonyl carbon of the fatty acid acyl.

2. The conjugate of claim 1, further comprising a dye.

3. The conjugate of claim 1, wherein the fatty acid acyl is a very long chain fatty acid or a long chain fatty acid acyl.

4. The conjugate of claim 3, wherein the long chain fatty acid acyl is palmitoyl.

5. The conjugate of claim 1, wherein $X_{23}$ is Phe; or $X_{23}$ is Trp; or $X_{11}$ is Leu and $X_{23}$ is Trp; or $X_{11}$ is Leu, $X_{13}$ is Lys, and $X_{23}$ is Trp.

6. The conjugate of claim 1, wherein the polypeptide has the amino acid sequence Leu-Nle-His-Gln-Leu-dTrp-Lys-Trp-Ile-Gln-Asp-Ala-Arg-Arg-Arg-Ala-Trp-Leu-His-Lys-Leu-Ile-Ala-Glu-Ile-His-Thr-Ala-Glu-Ile (SEQ ID NO: 5); or Leu-Nle-His-Gln-Leu-dTrp-Lys-Trp-Ile-Gln-Asp-Ala-Arg-Arg-Arg-Ala-Trp-Leu-Leu-Lys-Leu-Ile-Ala-Glu-Ile-His-Thr-Ala-Glu-Ile (SEQ ID NO: 7).

7. A pharmaceutical composition comprising the conjugate of claim 1 and one or more pharmaceutically acceptable carriers or excipients.

* * * * *

UNITED STATES PATENT AND TRADEMARK OFFICE
CERTIFICATE OF CORRECTION

PATENT NO. : 11,975,050 B2
APPLICATION NO. : 16/980944
DATED : May 7, 2024
INVENTOR(S) : Thomas J. Gardella et al.

It is certified that error appears in the above-identified patent and that said Letters Patent is hereby corrected as shown below:

In the Claims

Column 41, Claim 1, Line 31, replace "X10" with --$X_{10}$--.

Signed and Sealed this
Fourth Day of June, 2024

Katherine Kelly Vidal
*Director of the United States Patent and Trademark Office*